(12) United States Patent
Delaney et al.

(10) Patent No.: US 9,129,013 B2
(45) Date of Patent: Sep. 8, 2015

(54) METHODS AND APPARATUS FOR ENTITY DETECTION

(71) Applicant: Nuance Communications, Inc., Burlington, MA (US)

(72) Inventors: Brian W. Delaney, Bolton, MA (US); Girija Yegnanarayanan, Raleigh, NC (US)

(73) Assignee: Nuance Communications, Inc., Burlington, MA (US)

( * ) Notice: Subject to any disclaimer, the term of this patent is extended or adjusted under 35 U.S.C. 154(b) by 111 days.

(21) Appl. No.: 13/795,886

(22) Filed: Mar. 12, 2013

(65) Prior Publication Data
US 2014/0280353 A1  Sep. 18, 2014

(51) Int. Cl.
G06F 7/02 (2006.01)
G06F 17/30 (2006.01)
G06F 17/27 (2006.01)
G06F 19/00 (2011.01)

(52) U.S. Cl.
CPC ........ *G06F 17/30734* (2013.01); *G06F 17/278* (2013.01); *G06F 17/2785* (2013.01); *G06F 19/322* (2013.01)

(58) Field of Classification Search
CPC .......... G06F 17/2785; G06F 17/30734; G06N 99/005
See application file for complete search history.

(56) References Cited

U.S. PATENT DOCUMENTS

| 7,672,987 B2 * | 3/2010 | Mukherjee et al. ........... 707/776 |
| 8,843,497 B2 * | 9/2014 | Stankiewicz et al. ......... 707/740 |
| 8,898,140 B2 * | 11/2014 | Cooper et al. ................ 707/711 |

OTHER PUBLICATIONS

"Probabilistic Models for Topic Learning from Images and Captions in Online Biomedical Literatures," Chen, Xin et al, CIKM '09 Nov. 2-6, 2009 Hong Kong, China.*
Florian et al., "A Statistical Model for Multilingual Entity Detection and Tracking," Proceedings of the Human Language Technologies Conference 2004 (HLT-NAACL'04), (2004).
Salton et al., "A Vector Space Model for Automatic Indexing," Communications of the ACM, vol. 18, No. 11, Nov. 1975.
U.S. Appl. No. 11/322,971, filed Dec. 30, 2005, Zimmerman et al.
International Search Report and Written Opinion for PCT/US2014/018165 mailed Sep. 8, 2014.
Zhou et al., Approaches to text mining for clinical medical records. SAC '06 Proceedings of the 2006 ACM Symposium on Applied Computing. 2006:235-239.

* cited by examiner

*Primary Examiner* — Bruce Moser
(74) *Attorney, Agent, or Firm* — Wolf, Greenfield & Sacks, P.C.

(57) ABSTRACT

Techniques for entity detection include matching a token from at least a portion of a text string with a matching concept in an ontology. A first concept may be identified as being hierarchically related to the matching concept within the ontology, and a second concept may be identified as being hierarchically related to the first concept within the ontology. The first and second concepts may be included in a set of features of the token. Based at least in part on the set of features of the token, a measure related to a likelihood that the at least a portion of the text string corresponds to a particular entity type may be determined.

20 Claims, 12 Drawing Sheets

Patient Name: John Doe  Sex: M  Creation Date: 01-18-2011
Document Type: Discharge Summary Problems  Medications  Allergies  Social History  Procedures  Vital Signs    Show All Problems(4)
Add Fact
| | Name | Status |
|---|---|---|
| x | Unspecified Chest Pain | active |
| x | Shortness of Breath | active |
| x | Unspecified Essential Hypertension | history |
| x | Obesity Unspecified | history |

Medications(1)
Add Fact
| | Name | Status | Schedules |
|---|---|---|---|
| x | | | None |

Allergies(0)
Add Fact
| | Name | Type | Status |
|---|---|---|---|

Chief complaint: Patient is presenting chest pain and shortness of breath.

Medical history: The patient is hypertensive. He is also obese.

Social history: He smokes one pack per day. Drinks occasionally.

Save  Dictate  Complete  Cancel

METHODS AND APPARATUS FOR ENTITY DETECTION

BACKGROUND

1. Field

The techniques described herein are directed generally to the field of natural language understanding, and more particularly to techniques for entity detection.

2. Description of the Related Art

Medical documentation is an important process in the healthcare industry. Most healthcare institutions maintain a longitudinal medical record (e.g., spanning multiple observations or treatments over time) for each of their patients, documenting, for example, the patient's history, encounters with clinical staff within the institution, treatment received, and/or plans for future treatment. Such documentation facilitates maintaining continuity of care for the patient across multiple encounters with various clinicians over time. In addition, when an institution's medical records for large numbers of patients are considered in the aggregate, the information contained therein can be useful for educating clinicians as to treatment efficacy and best practices, for internal auditing within the institution, for quality assurance, etc.

Historically, each patient's medical record was maintained as a physical paper folder, often referred to as a "medical chart", or "chart". Each patient's chart would include a stack of paper reports, such as intake forms, history and immunization records, laboratory results and clinicians' notes. Following an encounter with the patient, such as an office visit, a hospital round or a surgical procedure, the clinician conducting the encounter would provide a narrative note about the encounter to be included in the patient's chart. Such a note could include, for example, a description of the reason(s) for the patient encounter, an account of any vital signs, test results and/or other clinical data collected during the encounter, one or more diagnoses determined by the clinician from the encounter, and a description of a plan for further treatment. Often, the clinician would verbally dictate the note into an audio recording device or a telephone giving access to such a recording device, to spare the clinician the time it would take to prepare the note in written form. Later, a medical transcriptionist would listen to the audio recording and transcribe it into a text document, which would be inserted on a piece of paper into the patient's chart for later reference.

Currently, many healthcare institutions are transitioning or have transitioned from paper documentation to electronic medical record systems, in which patients' longitudinal medical information is stored in a data repository in electronic form. Besides the significant physical space savings afforded by the replacement of paper record-keeping with electronic storage methods, the use of electronic medical records also provides beneficial time savings and other opportunities to clinicians and other healthcare personnel. For example, when updating a patient's electronic medical record to reflect a current patient encounter, a clinician need only document the new information obtained from the encounter, and need not spend time entering unchanged information such as the patient's age, gender, medical history, etc. Electronic medical records can also be shared, accessed and updated by multiple different personnel from local and remote locations through suitable user interfaces and network connections, eliminating the need to retrieve and deliver paper files from a crowded file room.

SUMMARY

One embodiment is directed to a method comprising: matching a token from at least a portion of a text string with a matching concept in an ontology; identifying a first concept as being hierarchically related to the matching concept within the ontology; identifying a second concept as being hierarchically related to the first concept within the ontology; including the first and second concepts in a set of features of the token; and determining, using at least one processor, a measure related to a likelihood that the at least a portion of the text string corresponds to a particular entity type, based at least in part on the set of features of the token.

Another embodiment is directed to apparatus comprising at least one processor, and at least one processor-readable storage medium storing processor-executable instructions that, when executed by the at least one processor, perform a method comprising: matching a token from at least a portion of a text string with a matching concept in an ontology; identifying a first concept as being hierarchically related to the matching concept within the ontology; identifying a second concept as being hierarchically related to the first concept within the ontology; including the first and second concepts in a set of features of the token; and determining a measure related to a likelihood that the at least a portion of the text string corresponds to a particular entity type, based at least in part on the set of features of the token.

Another embodiment is directed to at least one computer-readable storage medium encoded with computer-executable instructions that, when executed, perform a method comprising: matching a token from at least a portion of a text string with a matching concept in an ontology; identifying a first concept as being hierarchically related to the matching concept within the ontology; identifying a second concept as being hierarchically related to the first concept within the ontology; including the first and second concepts in a set of features of the token; and determining a measure related to a likelihood that the at least a portion of the text string corresponds to a particular entity type, based at least in part on the set of features of the token.

Another embodiment is directed to a method comprising: matching a token from at least a portion of a text string with a matching concept in an ontology, wherein the at least a portion of the text string has been labeled as corresponding to a particular entity type; identifying a first concept as being hierarchically related to the matching concept within the ontology; identifying a second concept as being hierarchically related to the first concept within the ontology; and training, using at least one processor, a statistical model to associate the first concept with a first probability of corresponding to the particular entity type and the second concept with a second probability of corresponding to the particular entity type, based at least in part on the labeling of the at least a portion of the text string as corresponding to the particular entity type.

Another embodiment is directed to apparatus comprising at least one processor, and at least one processor-readable storage medium storing processor-executable instructions that, when executed by the at least one processor, perform a method comprising: matching a token from at least a portion of a text string with a matching concept in an ontology, wherein the at least a portion of the text string has been labeled as corresponding to a particular entity type; identifying a first concept as being hierarchically related to the matching concept within the ontology; identifying a second concept as being hierarchically related to the first concept within the ontology; and training a statistical model to associate the first concept with a first probability of corresponding to the particular entity type and the second concept with a second probability of corresponding to the particular entity type, based at least in part on the labeling of the at least a portion of the text string as corresponding to the particular entity type.

Another embodiment is directed to at least one computer-readable storage medium encoded with computer-executable instructions that, when executed, perform a method comprising: matching a token from at least a portion of a text string with a matching concept in an ontology, wherein the at least a portion of the text string has been labeled as corresponding to a particular entity type; identifying a first concept as being hierarchically related to the matching concept within the ontology; identifying a second concept as being hierarchically related to the first concept within the ontology; and training a statistical model to associate the first concept with a first probability of corresponding to the particular entity type and the second concept with a second probability of corresponding to the particular entity type, based at least in part on the labeling of the at least a portion of the text string as corresponding to the particular entity type.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 3A and 3B are screenshots illustrating an exemplary display of medical facts in a user interface in accordance with some embodiments of the present invention;

FIG. 4 is a screenshot illustrating an exemplary display of linkage between text and a clinical fact in accordance with some embodiments of the present invention;

DETAILED DESCRIPTION

Figure 1:
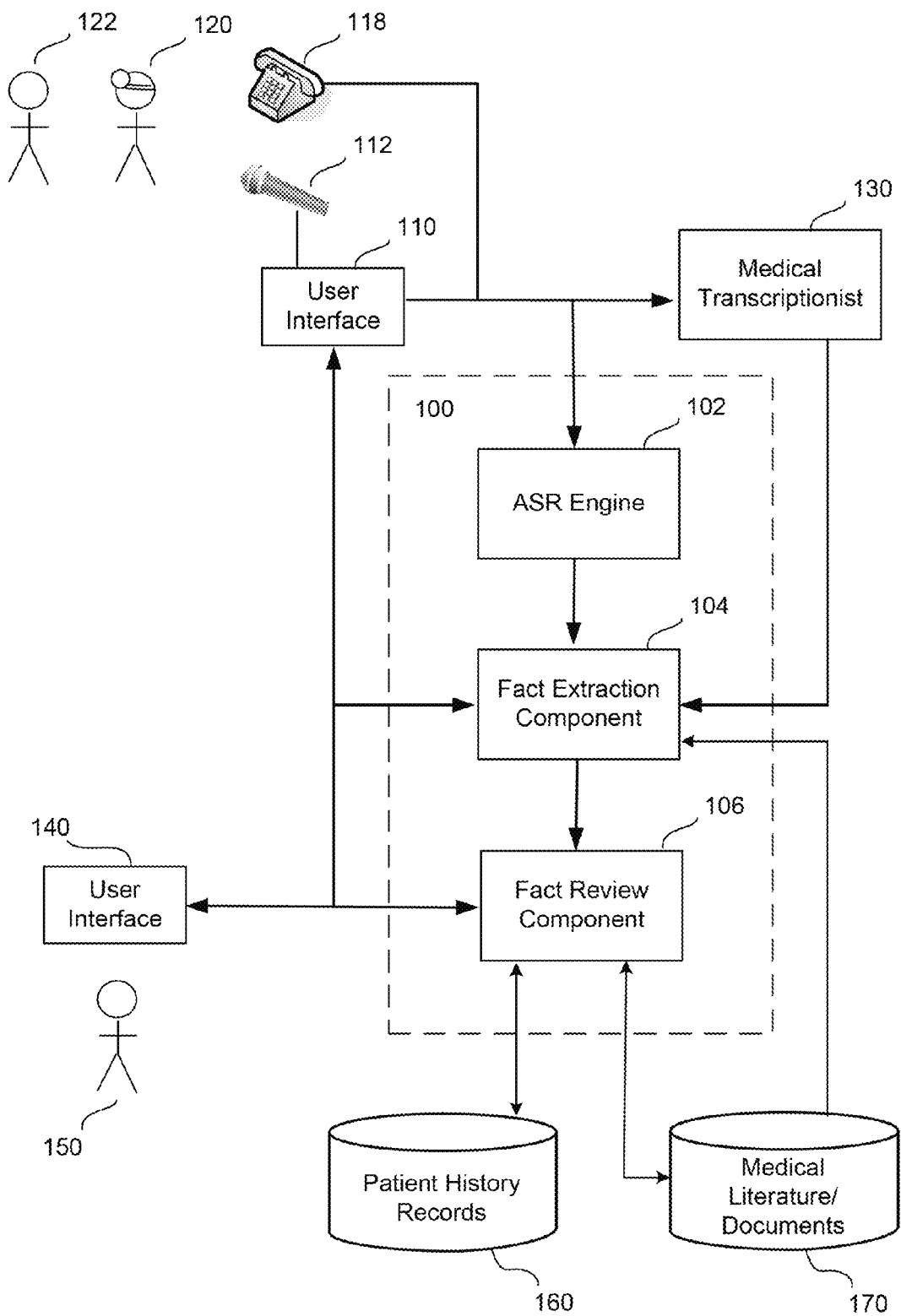
FIG. 1 is a block diagram of an exemplary operating environment for a system in accordance with some embodiments of the present invention.

An Electronic Health Record (EHR) is an electronic medical record that generally is maintained by a specific healthcare institution and contains data documenting the care that a specific patient has received from that institution over time. Typically, an EHR is maintained as a structured data representation, such as a database with structured fields. Each piece of information stored in such an EHR is typically represented as a discrete (e.g., separate) data item occupying a field of the EHR database. For example, a 55-year old male patient named John Doe may have an EHR database record with "John Doe" stored in the patient_name field, "55" stored in the patient_age field, and "Male" stored in the patient_gender field. Data items or fields in such an EHR are structured in the sense that only a certain limited set of valid inputs is allowed for each field. For example, the patient_name field may require an alphabetic string as input, and may have a maximum length limit; the patient_age field may require a string of three numerals, and the leading numeral may have to be "0" or "1"; the patient_gender field may only allow one of two inputs, "Male" and "Female"; a patient_birth_date field may require input in a "MM/DD/YYYY" format; etc.

Typical EHRs are also structured in terms of the vocabulary they use, as medical terms are normalized to a standard set of terms utilized by the institution maintaining the EHR. The standard set of terms may be specific to the institution, or may be a more widely used standard. For example, a clinician dictating or writing a free-form note may use any of a number of different terms for the condition of a patient currently suffering from an interruption of blood supply to the heart, including "heart attack", "acute myocardial infarction", "acute MI" and "AMI". To facilitate interoperability of EHR data between various departments and users in the institution, and/or to allow identical conditions to be identified as such across patient records for data analysis, a typical EHR may use only one standardized term to represent each individual medical concept. For example, "acute myocardial infarction" may be the standard term stored in the EHR for every case of a heart attack occurring at the time of a clinical encounter. Some EHRs may represent medical terms in a data format corresponding to a coding standard, such as the International Classification of Disease (ICD) standard. For example, "acute myocardial infarction" may be represented in an EHR as "ICD-9 410", where 410 is the code number for "acute myocardial infarction" according to the ninth edition of the ICD standard.

To allow clinicians and other healthcare personnel to enter medical documentation data directly into an EHR in its discrete structured data format, many EHRs are accessed through user interfaces that make extensive use of point-and-click input methods. While some data items, such as the patient's name, may require input in (structured) textual or numeric form, many data items can be input simply through the use of a mouse or other pointing input device (e.g., a touch screen) to make selections from pre-set options in drop-down menus and/or sets of checkboxes and/or radio buttons or the like.

The inventors have recognized, however, that while some clinicians may appreciate the ability to directly enter structured data into an EHR through a point-and-click interface, many clinicians may prefer being unconstrained in what they can say and in what terms they can use in a free-form note, and many may be reluctant to take the time to learn where all the boxes and buttons are and what they all mean in an EHR user interface. In addition, many clinicians may prefer to take advantage of the time savings that can be gained by providing notes through verbal dictation, as speech can often be a faster form of data communication than typing or clicking through forms.

Accordingly, some embodiments described herein relate to techniques for enhancing the creation and use of structured electronic medical records, using techniques that enable a clinician to provide input and observations via a free-form narrative clinician's note. Some embodiments involve the automatic extraction of discrete medical facts (e.g., clinical facts), such as could be stored as discrete structured data items in an electronic medical record, from a clinician's free-form narration of a patient encounter. In some embodiments, the extraction of medical facts may involve improved techniques for entity detection, which involves the processing of text to identify mentions of particular things (entities) of interest (e.g., medical facts), despite variations in the terms people use to express those things. In some embodiments, free-form input may be provided, but the advantages of storage, maintenance and accessing of medical documentation data in electronic forms may be maintained. For example, the storage of a patient's medical documentation data as a collection of discrete structured data items may provide the benefits of being able to query for individual data items of interest, and being able to assemble arbitrary subsets of the patient's data items into new reports, orders, invoices, etc., in an automated and efficient manner.

In some embodiments, pre-processing may be performed on a free-form narration prior to performing automatic fact extraction, to determine the sequence of words represented by the free-form narration. Such pre-processing may also be performed in any suitable way using any suitable technique(s), as aspects of the present invention are not limited in this respect. For example, in some embodiments, the clinician may provide the free-form narration directly in textual form (e.g., using a keyboard or other text entry device), and the textual free-form narration may be automatically parsed to determine its sequence of words. In other embodiments, the clinician may provide the free-form narration in audio form as a spoken dictation, and an audio recording of the clinician's spoken dictation may be received and/or stored. The audio input may be processed in any suitable way prior to or in the process of performing fact extraction, as aspects of the invention are not limited in this respect. In some embodiments, the audio input may be processed to form a textual representation, and fact extraction may be performed on the textual representation. Such processing to produce a textual representation may be performed in any suitable way. For example, in some embodiments, the audio recording may be transcribed by a human transcriptionist, while in other embodiments, automatic speech recognition (ASR) may be performed on the audio recording to obtain a textual representation of the free-form narration provided via the clinician's dictation. Any suitable automatic speech recognition technique may be used, as aspects of the present invention are not limited in this respect. In other embodiments, speech-to-text conversion of the clinician's audio dictation may not be required, as a technique that does not involve processing the audio to produce a textual representation may be used to determine what was spoken. In one example, the sequence of words that was spoken may be determined directly from the audio recording, e.g., by comparing the audio recording to stored waveform templates to determine the sequence of words. In other examples, the clinician's speech may not be recognized as words, but may be recognized in another form such as a sequence or collection of abstract concepts. It should be appreciated that the words and/or concepts represented in the clinician's free-form narration may be represented and/or stored as data in any suitable form, including forms other than a textual representation, as aspects of the present invention are not limited in this respect.

In some embodiments, one or more medical facts may be automatically extracted from the free-form narration (in audio or textual form) or from a pre-processed data representation of the free-form narration using a fact extraction component applying natural language understanding techniques. In some embodiments, the medical facts to be extracted may be defined by a set of fact categories (also referred to herein as "fact types" or "entity types") commonly used by clinicians in documenting patient encounters. In some embodiments, a suitable set of fact categories may be defined by any of various known healthcare standards. For example, in some embodiments, the medical facts to be extracted may include facts that are required to be documented by Meaningful Use standards promulgated by the U.S. government, e.g., under 42 C.F.R. §495, which sets forth "Objectives" specifying items of medical information to be recorded for medical patients. Such facts currently required by the Meaningful Use standards include social history facts, allergy facts, diagnostic test result facts, medication facts, problem facts, procedure facts, and vital sign facts. However, these are merely exemplary, as aspects of the invention are not limited to any particular set of fact categories. Some embodiments may not use one or more of the above-listed fact categories, and some embodiments may use any other suitable fact categories. Other non-limiting examples of suitable categories of medical facts include findings, disorders, body sites, medical devices, subdivided categories such as observable findings and measurable findings, etc. The fact extraction component may be implemented in any suitable form, as aspects of the present invention are not limited in this respect. Exemplary implementations for a fact extraction component are described in detail below.

One illustrative application for the techniques described herein is for use in a system for enhancing medical documentation processes. An exemplary operating environment for such a system is illustrated in FIG. 1. The exemplary operating environment includes a medical documentation system 100, which may be implemented in any suitable form, as aspects of the present invention are not limited in this respect. For example, system 100 may be implemented as a single stand-alone machine, or may be implemented by multiple distributed machines that share processing tasks in any suitable manner. System 100 may be implemented as one or more computers; an example of a suitable computer is described below. In some embodiments, system 100 may include one or more tangible, non-transitory computer-readable storage devices storing processor-executable instructions, and one or more processors that execute the processor-executable instructions to perform the functions described herein. The storage devices may be implemented as computer-readable storage media encoded with the processor-executable instructions; examples of suitable computer-readable storage media are discussed below.

As depicted, exemplary system 100 includes an ASR engine 102, a fact extraction component 104, and a fact review component 106. Each of these processing components of system 100 may be implemented in software, hardware, or a combination of software and hardware. Components implemented in software may comprise sets of processor-executable instructions that may be executed by the one or more processors of system 100 to perform the functionality described herein. Each of ASR engine 102, fact extraction component 104 and fact review component 106 may be implemented as a separate component of system 100, or any combination of these components may be integrated into a single component or a set of distributed components. In addition, any one of ASR engine 102, fact extraction component 104 and fact review component 106 may be implemented as a set of multiple software and/or hardware components. It should be understood that any such component depicted in FIG. 1 is not limited to any particular software and/or hardware implementation and/or configuration.

As illustrated in FIG. 1, user interface 110 is presented to a clinician 120, who may be a physician, a physician's aide, a nurse, or any other personnel involved in the evaluation and/ or treatment of a patient 122 in a clinical setting. During the course of a clinical encounter with patient 122, or at some point thereafter, clinician 120 may wish to document the patient encounter. Such a patient encounter may include any interaction between clinician 120 and patient 122 in a clinical evaluation and/or treatment setting, including, but not limited to, an office visit, an interaction during hospital rounds, an outpatient or inpatient procedure (surgical or non-surgical), a follow-up evaluation, a visit for laboratory or radiology testing, etc. One method that clinician 120 may use to document the patient encounter may be to enter medical facts that can be ascertained from the patient encounter into user interface 110 as discrete structured data items. The set of medical facts, once entered, may be transmitted in some embodiments via any suitable communication medium or media (e.g., local and/or network connection(s) that may include wired and/or wireless connection(s)) to system 100. Specifically, in some embodiments, the set of medical facts may be received at system 100 by a fact review component 106, exemplary functions of which are described below.

Another method that may be used by clinician 120 to document the patient encounter is to provide a free-form narration of the patient encounter. In some embodiments, the narration may be free-form in the sense that clinician 120 may be unconstrained with regard to the structure and content of the narration, and may be free to provide any sequence of words, sentences, paragraphs, sections, etc., that he would like. In some embodiments, there may be no limitation on the length of the free-form narration, or the length may be limited only by the processing capabilities of the user interface into which it is entered or of the later processing components that will operate upon it. In other embodiments, the free-form narration may be constrained in length (e.g., limited to a particular number of characters).

A free-form narration of the patient encounter may be provided by clinician 120 in any of various ways. One way may be to manually enter the free-form narration in textual form into user interface 110, e.g., using a keyboard. In this respect, the one or more processors of system 100 and/or of a client device in communication with system 100 may in some embodiments be programmed to present a user interface including a text editor/word processor to clinician 120. Such a text editor/word processor may be implemented in any suitable way, as aspects of the present invention are not limited in this respect.

Another way to provide a free-form narration of the patient encounter may be to verbally speak a dictation of the patient encounter. Such a spoken dictation may be provided in any suitable way, as aspects of the present invention are not limited in this respect. As illustrated in FIG. 1, one way that clinician 120 may provide a spoken dictation of the free-form narration may be to speak the dictation into a microphone 112 providing input (e.g., via a direct wired connection, a direct wireless connection, or via a connection through an intermediate device) to user interface 110. An audio recording of the spoken dictation may then be stored in any suitable data format, and transmitted to system 100 and/or to medical transcriptionist 130. Another way that clinician 120 may provide the spoken dictation may be to speak into a telephone 118, from which an audio signal may be transmitted to be recorded at system 100, at the site of medical transcriptionist 130, or at any other suitable location. Alternatively, the audio signal may be recorded in any suitable data format at an intermediate facility, and the audio data may then be relayed to system 100 and/or to medical transcriptionist 130.

In some embodiments, medical transcriptionist 130 may receive the audio recording of the dictation provided by clinician 120, and may transcribe it into a textual representation of the free-form narration (e.g., into a text narrative). Medical transcriptionist 130 may be any human who listens to the audio dictation and writes or types what was spoken into a text document. In some embodiments, medical transcriptionist 130 may be specifically trained in the field of medical transcription, and may be well-versed in medical terminology. In some embodiments, medical transcriptionist 130 may transcribe exactly what she hears in the audio dictation, while in other embodiments, medical transcriptionist 130 may add formatting to the text transcription to comply with generally accepted medical document standards. When medical transcriptionist 130 has completed the transcription of the free-form narration into a textual representation, the resulting text narrative may in some embodiments be transmitted to system 100 or any other suitable location (e.g., to a storage location accessible to system 100). Specifically, in some embodiments the text narrative may be received from medical transcriptionist 130 by fact extraction component 104 within system 100. Exemplary functionality of fact extraction component 104 is described below.

In some other embodiments, the audio recording of the spoken dictation may be received, at system 100 or any other suitable location, by automatic speech recognition (ASR) engine 102. In some embodiments, ASR engine 102 may then process the audio recording to determine what was spoken. As discussed above, such processing may involve any suitable speech recognition technique, as aspects of the present invention are not limited in this respect. In some embodiments, the audio recording may be automatically converted to a textual representation, while in other embodiments, words identified directly from the audio recording may be represented in a data format other than text, or abstract concepts may be identified instead of words. Examples of further processing are described below with reference to a text narrative that is a textual representation of the free-form narration; however, it should be appreciated that similar processing may be performed on other representations of the free-form narration as discussed above. When a textual representation is produced, in some embodiments it may be reviewed by a human (e.g., a transcriptionist) for accuracy, while in other embodiments the output of ASR engine 102 may be accepted as accurate without human review. As discussed above, some embodiments are not limited to any particular method for transcribing audio data; an audio recording of a spoken dictation may be transcribed manually by a human transcriptionist, automatically by ASR, or semiautomatically by human editing of a draft transcription produced by ASR. Transcriptions produced by ASR engine 102 and/or by transcriptionist 130 may be encoded or otherwise represented as data in any suitable form, as aspects of the invention are not limited in this respect.

In some embodiments, ASR engine 102 may make use of a lexicon of medical terms (which may be part of, or in addition to, another more general speech recognition lexicon) while determining the sequence of words that were spoken in the free-form narration provided by clinician 120. However, aspects of the invention are not limited to the use of a lexicon, or any particular type of lexicon, for ASR. When used, the medical lexicon in some embodiments may be linked to a knowledge representation model such as a clinical language understanding ontology utilized by fact extraction component 104, such that ASR engine 102 might produce a text narrative containing terms in a form understandable to fact extraction component 104. In some embodiments, a more general speech recognition lexicon might also be shared between ASR engine 102 and fact extraction component 104.

However, in other embodiments, ASR engine 102 may not have any lexicon developed to be in common with fact extraction component 104. In some embodiments, a lexicon used by ASR engine 102 may be linked to a different type of medical knowledge representation model, such as one not designed or used for language understanding. It should be appreciated that any lexicon used by ASR engine 102 and/or fact extraction component 104 may be implemented and/or represented as data in any suitable way, as aspects of the invention are not limited in this respect.

In some embodiments, a text narrative, whether produced by ASR engine 102 (and optionally verified or not by a human), produced by medical transcriptionist 130, directly entered in textual form through user interface 110, or produced in any other way, may be re-formatted in one or more ways before being received by fact extraction component 104. Such re-formatting may be performed by ASR engine 102, by a component of fact extraction component 104, by a combination of ASR engine 102 and fact extraction component 104, or by any other suitable software and/or hardware component. In some embodiments, the re-formatting may be performed in a way known to facilitate fact extraction, and may be performed for the purpose of facilitating the extraction of clinical facts from the text narrative by fact extraction component 104. For example, in some embodiments, processing to perform fact extraction may be improved if sentence boundaries in the text narrative are accurate. Accordingly, in some embodiments, the text narrative may be re-formatted prior to fact extraction to add, remove or correct one or more sentence boundaries within the text narrative. In some embodiments, this may involve altering the punctuation in at least one location within the text narrative. In another example, fact extraction may be improved if the text narrative is organized into sections with headings, and thus the re-formatting may include determining one or more section boundaries in the text narrative and adding, removing or correcting one or more corresponding section headings. In some embodiments, the re-formatting may include normalizing one or more section headings (which may have been present in the original text narrative and/or added or corrected as part of the re-formatting) according to a standard for the healthcare institution corresponding to the patient encounter (which may be an institution-specific standard or a more general standard for section headings in clinical documents). In some embodiments, a user (such as clinician 120, medical transcriptionist 130, or another user) may be prompted to approve the re-formatted text.

Any suitable technique(s) for implementing re-formatting, examples of which are described above, may be employed, as aspects of the invention are not limited in this respect. One exemplary technique suitable for performing re-formatting of a text narrative is described in U.S. patent application Ser. No. 11/322,971, filed on Dec. 30, 2005, entitled "Translating Literal Speech to Formatted Text", which is incorporated herein by reference in its entirety. Another exemplary technique that may be used in some embodiments for performing re-formatting of a text narrative involves the use of word N-gram statistical models to predict sentence and/or section boundaries in a text narrative. Such statistical models may be trained on a corpus of documents (e.g., past medical records) with correct punctuation and/or section headings (e.g., supplied by a medical transcriptionist).

In some embodiments, a statistical model may add punctuation (e.g., periods, exclamation points, question marks, etc.) to add one or more sentence boundaries to a text narrative by computing a probability, for each word in the text narrative, that a particular punctuation mark should follow that word. In computing the probability that a word should be followed by a punctuation mark, the statistical model may consider the N-word sequence from the text narrative that ends with that word, and determine the frequency with which that N-word sequence is followed by that punctuation mark in the training data for the statistical model. A lattice may then be constructed using the computed probabilities for all the words in the text narrative, or in a portion of the text narrative, and the best path in terms of combined probability through the lattice may be determined. Where punctuation marks are located in the best path through the lattice, those punctuation marks may be added in those locations to the text narrative in producing the formatted text. In some embodiments, another statistical model may add section headings, corresponding to section boundaries, in a similar fashion. For example, in some embodiments, a statistical model for section headings may compute probabilities, for each word, that the word should be followed by a section boundary. In some embodiments, in computing probabilities, a statistical model for section headings may consider more words that follow the current word than words that precede the current word. In some embodiments, one or more separate statistical models may be trained to delete incorrect sentence and/or section boundaries. Those models may in some embodiments be trained through feedback from clinician 120 or another user, by observing word sequences (initially including punctuation and/or section boundaries) from which clinician 120 or another user tends to remove the punctuation and/or section boundaries when editing.

In some embodiments, either an original or a re-formatted text narrative may be received by fact extraction component 104, which may perform processing to extract one or more medical facts from the text narrative. The text narrative may be received from ASR engine 102, from medical transcriptionist 130, directly from clinician 120 via user interface 110, or in any other suitable way. Exemplary techniques for medical fact extraction are described below.

In some embodiments, a fact extraction component may make use of one or more ontologies linked to one or more lexicons of medical terms. An ontology may be implemented as a relational database, or in any other suitable form, and may represent semantic concepts relevant to the medical domain. In some embodiments, such an ontology may also represent linguistic concepts related to ways the semantic concepts may be expressed in natural language.

In some embodiments, concepts in an ontology used by a fact extraction component may be linked to a lexicon of medical terms and/or codes, such that each medical term and each code is linked to at least one concept in the formal ontology. In some embodiments, the lexicon may include the standard medical terms and/or codes used by the institution in which the fact extraction component is applied. For example, the standard medical terms and/or codes used by an EHR maintained by the institution may be included in the lexicon linked to an ontology. In some embodiments, the lexicon may also include additional medical terms used by the various clinicians within the institution, and/or used by clinicians generally, when describing medical issues in a free-form narration. Such additional medical terms may be linked, along with their corresponding standard medical terms, to the appropriate shared concepts within the ontology. For example, the standard term "acute myocardial infarction" as well as other corresponding terms such as "heart attack", "acute MI" and "AMI" may all be linked to the same concept in the ontology—a concept representing an interruption of blood supply to the heart. Such linkage of multiple medical terms to the same concept in some embodiments may relieve the clinician of the burden of ensuring that only standard medical terms preferred by the institution appear in the free-form narration. For example, in some embodiments, a clinician may be free to use the abbreviation "AMI" or the colloquial "heart attack" in his free-form narration, and the shared concept linkage may allow the fact extraction component to nevertheless automatically extract a fact corresponding to "acute myocardial infarction".

In some embodiments, an ontology used by a fact extraction component may also represent various types of relationships between the concepts represented. One type of relationship between two concepts may be a parent-child relationship (also called a hypernym-hyponym relationship), in which the child concept is a more specific version of the parent concept. More formally, in a parent-child relationship, the child concept inherits all necessary properties of the parent concept, while the child concept may have necessary properties that are not shared by the parent concept. For example, "heart failure" may be a parent concept, and "congestive heart failure" may be a child concept of "heart failure." Parent-child relationships, or equivalently hypernym-hyponym relationships, are also often referred to as "is-a" relationships, reflecting the fact that the hyponym (the child) is a type of the hypernym (the parent) (e.g., "congestive heart failure" is a type of "heart failure"). In some embodiments, any other type(s) of relationship useful to the process of medical documentation may also be represented in an ontology. For example, one type of relationship may be a symptom relationship. In one example of a symptom relationship, a concept linked to the term "chest pain" may have a relationship of "is-symptom-of" to the concept linked to the term "heart attack". Other types of relationships may include complication relationships, comorbidity relationships, interaction relationships (e.g., among medications), and many others. Any number and type(s) of concept relationships may be included in such an ontology, as aspects of the present invention are not limited in this respect.

Alternatively or additionally, in some embodiments a fact extraction component may make use of one or more statistical models to extract semantic entities from natural language input. In general, a statistical model can be described as a functional component designed and/or trained to analyze new inputs based on probabilistic patterns observed in prior training inputs. In this sense, statistical models differ from "rule-based" models, which typically apply hard-coded deterministic rules to map from inputs having particular characteristics to particular outputs. By contrast, a statistical model may operate to determine a particular output for an input with particular characteristics by considering how often (e.g., with what probability) training inputs with those same characteristics (or similar characteristics) were associated with that particular output in the statistical model's training data. To supply the probabilistic data that allows a statistical model to extrapolate from the tendency of particular input characteristics to be associated with particular outputs in past examples, statistical models are typically trained (or "built") on large training corpuses with great numbers of example inputs. Typically the example inputs are labeled with the known outputs with which they should be associated, usually by a human labeler with expert knowledge of the domain. Characteristics of interest (known as "features") are identified ("extracted") from the inputs, and the statistical model learns the probabilities with which different features are associated with different outputs, based on how often training inputs with those features are associated with those outputs. When the same features are extracted from a new input (e.g., an input that has not been labeled with a known output by a human), the statistical model can then use the learned probabilities for the extracted features (as learned from the training data) to determine which output is most likely correct for the new input. Exemplary implementations of a fact extraction component using one or more statistical models are described further below.

In some embodiments, fact extraction component 104 may utilize a statistical fact extraction model based on entity detection and/or tracking techniques, such as those disclosed in: Florian, R., Hassan, H., Ittycheriah, A., Jing, H., Kambhatla, N., Luo, X., Nicolov, N., and Roukos, S. (2004). *A Statistical Model for Multilingual Entity Detection and Tracking*. Proceedings of the Human Language Technologies Conference 2004 (HLT-NAACL'04). This publication is incorporated herein by reference in its entirety.

For example, in some embodiments, a list of fact types of interest for generating medical reports may be defined, e.g., by a developer of fact extraction component 104. Such fact types (also referred to herein as "entity types") may include, for example, problems, disorders (a disorder is a type of problem), diagnoses (a diagnosis may be a disorder that a clinician has identified as a problem for a particular patient), findings (a finding is a type of problem that need not be a disorder), medications, body sites, social history facts, allergies, diagnostic test results, vital signs, procedures, procedure steps, observations, devices, and/or any other suitable medical fact types. It should be appreciated that any suitable list of fact types may be utilized, and may or may not include any of the fact types listed above, as aspects of the invention are not limited in this respect. In some embodiments, spans of text in a set of sample patient encounter reports may be labeled (e.g., by a human) with appropriate fact types from the list. A statistical model may then be trained on the corpus of labeled sample reports to detect and/or track such fact types as semantic entities, using entity detection and/or tracking techniques, examples of which are described below.

For example, in some embodiments, a large number of past free-form narrations created by clinicians may be manually labeled to form a corpus of training data for a statistical entity detection model. As discussed above, in some embodiments, a list of suitable entities may be defined (e.g., by a domain administrator) to include medical fact types that are to be extracted from future clinician narrations. One or more human labelers (e.g., who may have specific knowledge about medical information and typical clinician narration content) may then manually label portions of the training texts with the particular defined entities to which they correspond. For example, given the training text, "Patient is complaining of acute sinusitis," a human labeler may label the text portion "acute sinusitis" with the entity label "Problem." In another example, given the training text, "He has sinusitis, which appears to be chronic," a human labeler may label the text "sinusitis" and "chronic" with a single label indicating that both words together correspond to a "Problem" entity. As should be clear from these examples, the portion of the text labeled as corresponding to a single conceptual entity need not be formed of contiguous words, but may have words split up within the text, having non-entity words in between.

In some embodiments, the labeled corpus of training data may then be processed to build a statistical model trained to detect mentions of the entities labeled in the training data. Each time the same conceptual entity appears in a text, that appearance is referred to as a mention of that entity. For example, consider the text, "Patient has sinusitis. His sinusitis appears to be chronic." In this example, the entity detection model may be trained to identify each appearance of the word "sinusitis" in the text as a separate mention of the same "Problem" entity.

In some embodiments, the process of training a statistical entity detection model on labeled training data may involve a number of steps to analyze each training text and probabilistically associate its characteristics with the corresponding entity labels. In some embodiments, each training text (e.g., free-form clinician narration) may be tokenized to break it down into various levels of syntactic substructure. For example, in some embodiments, a tokenizer module may be implemented to designate spans of the text as representing structural/syntactic units such as document sections, paragraphs, sentences, clauses, phrases, individual tokens, words, sub-word units such as affixes, etc. In some embodiments, individual tokens may often be single words, but some tokens may include a sequence of more than one word that is defined, e.g., in a dictionary, as a token. For example, the term "myocardial infarction" could be defined as a token, although it is a sequence of more than one word. In some embodiments, a token's identity (i.e., the word or sequence of words itself) may be used as a feature of that token. In some embodiments, the token's placement within particular syntactic units in the text (e.g., its section, paragraph, sentence, etc.) may also be used as features of the token.

In some embodiments, an individual token within the training text may be analyzed (e.g., in the context of the surrounding sentence) to determine its part of speech (e.g., noun, verb, adjective, adverb, preposition, etc.), and the token's part of speech may be used as a further feature of that token. In some embodiments, each token may be tagged with its part of speech, while in other embodiments, not every token may be tagged with a part of speech. In some embodiments, a list of relevant parts of speech may be pre-defined, e.g., by a developer of the statistical model, and any token having a part of speech listed as relevant may be tagged with that part of speech. In some embodiments, a parser module may be implemented to determine the syntactic structure of sentences in the text, and to designate positions within the sentence structure as features of individual tokens. For example, in some embodiments, the fact that a token is part of a noun phrase or a verb phrase may be used as a feature of that token. Any type of parser may be used, non-limiting examples of which include a bottom-up parser and/or a dependency parser, as aspects of the invention are not limited in this respect.

In some embodiments, section membership may be used as a feature of a token. In some embodiments, a section normalization module may be implemented to associate various portions of the narrative text with the proper section to which it should belong.

In some embodiments, a set of standardized section types (e.g., identified by their section headings) may be defined for all texts, or a different set of normalized section headings may be defined for each of a number of different types of texts (e.g., corresponding to different types of documents). For example, in some embodiments, a different set of normalized section headings may be defined for each type of medical document in a defined set of medical document types. Non-limiting examples of medical document types include consultation reports, history & physical reports, discharge summaries, and emergency room reports, although there are also many other examples. In the medical field, the various types of medical documents are often referred to as "work types." In some cases, the standard set of sections for various types of medical documents may be established by a suitable system standard, institutional standard, or more widely applicable standard, such as the Meaningful Use standard (discussed above) or the Logical Observation Identifiers Names and Codes (LOINC) standard maintained by the Regenstrief Institute. For example, an expected set of section headings for a history & physical report under the Meaningful Use standard may include headings for a "Reason for Visit" section, a "History of Present Illness" section, a "History of Medication Use" section, an "Allergies, Adverse Reactions and Alerts" section, a "Review of Systems" section, a "Social History" section, a "Physical Findings" section, an "Assessment and Plan" section, and/or any other suitable section(s). Any suitable set of sections may be used, however, as aspects of the invention are not limited in this respect.

A section normalization module may use any suitable technique to associate portions of text with normalized document sections, as aspects of the invention are not limited in this respect. In some embodiments, the section normalization module may use a table (e.g., stored as data in a storage medium) to map text phrases that commonly occur in medical documents to the sections to which they should belong. In another example, a statistical model may be trained to determine the most likely section for a portion of text based on its semantic content, the semantic content of surrounding text portions, and/or the expected semantic content of the set of normalized sections. In some embodiments, once a normalized section for a portion of text has been identified, the membership in that section may be used as a feature of one or more tokens in that portion of text.

In some embodiments, other types of features may be extracted, i.e., identified and associated with tokens in the training text. For example, in some embodiments, an N-gram feature may identify the previous (N−1) words and/or tokens in the text as a feature of the current token. In another example, affixes (e.g., suffixes such as -ectomy, -oma, -itis, etc.) may be used as features of tokens. In another example, one or more predefined dictionaries and/or ontologies may be accessed, and a token's membership in any of those dictionaries may be used as a feature of that token. For example, a predefined dictionary of surgical procedures may be accessed, and/or a dictionary of body sites, and/or a dictionary of known diseases, etc. In some embodiments, related concepts in an ontology may be used as features of a token, as described further below. It should be appreciated, however, that all of the foregoing feature types are merely examples, and any suitable number and/or types of features of interest may be designated, e.g., by a developer of the statistical entity detection model, as aspects of the invention are not limited in this respect.

In some embodiments, the corpus of training text with its hand-labeled fact type entity labels, along with the collection of features extracted for tokens in the text, may be input to the statistical entity detection model for training. As discussed above, examples of suitable features include position within document structure, syntactic structure, parts of speech, parser features, N-gram features, affixes (e.g., prefixes and/or suffixes), membership in dictionaries (sometimes referred to as "gazetteers") and/or ontologies, surrounding token contexts (e.g., a certain number of tokens to the left and/or right of the current token), orthographic features (e.g., capitalization, letters vs. numbers, etc.), entity labels assigned to previous tokens in the text, etc. As one non-limiting example, consider the training sentence, "Patient is complaining of acute sinusitis," for which the word sequence "acute sinusitis" was hand-labeled as being a "Problem" entity. In one exemplary implementation, features extracted for the token "sinusitis" may include the token identity feature that the word is "sinusitis," a syntactic feature specifying that the token occurred at the end of a sentence (e.g., followed by a period), a part-of-speech feature of "noun," a parser feature that the token is part of a noun phrase ("acute sinusitis"), a trigram feature that the two preceding words are "of acute," an affix feature of "-itis," and a dictionary feature that the token is a member of a predefined dictionary of types of inflammation. It should be appreciated, however, that the foregoing list of features is merely exemplary, as any suitable features may be used. Aspects of the invention are not limited to any of the features listed above, and implementations including some, all, or none of the above features, as well as implementations including features not listed above, are possible.

In some embodiments, given the extracted features and manual entity labels for the entire training corpus as input, the statistical entity detection model may be trained to be able to probabilistically label new texts (e.g., texts not included in the training corpus) with automatic entity labels using the same feature extraction technique that was applied to the training corpus. In other words, by processing the input features and manual entity labels of the training corpus, the statistical model may learn probabilistic relationships between the features and the entity labels. When later presented with an input text without manual entity labels, the statistical model may then apply the same feature extraction techniques to extract features from the input text, and may apply the learned probabilistic relationships to automatically determine the most likely entity labels for word sequences in the input text. Any suitable statistical modeling technique may be used to learn such probabilistic relationships, as aspects of the invention are not limited in this respect. Non-limiting examples of suitable known statistical modeling techniques include machine learning techniques such as maximum entropy modeling, support vector machines, and conditional random fields, among others.

In some embodiments, training the statistical entity detection model may involve learning, for each extracted feature, a probability with which tokens having that feature are associated with each entity type. For example, for the suffix feature "-itis," the trained statistical entity detection model may store a probability p1 that a token with that feature should be labeled as being part of a "Problem" entity, a probability p2 that a token with that feature should be labeled as being part of a "Medication" entity, etc. In some embodiments, such probabilities may be learned by determining the frequency with which tokens having the "-itis" feature were hand-labeled with each different entity label in the training corpus. In some embodiments, the probabilities may be normalized such that, for each feature, the probabilities of being associated with each possible entity (fact type) may sum to 1. However, aspects of the invention are not limited to such normalization. In some embodiments, each feature may also have a probability p0 of not being associated with any fact type, such that the non-entity probability p0 plus the probabilities of being associated with each possible fact type sum to 1 for a given feature. In other embodiments, separate classifiers may be trained for each fact type, and the classifiers may be run in parallel. For example, the "-itis" feature may have probability p1 of being part of a "Problem" entity and probability (1−p1) of not being part of a "Problem" entity, probability p2 of being part of a "Medication" entity and probability (1−p2) of not being part of a "Medication" entity, and so on. In some embodiments, training separate classifiers may allow some word sequences to have a non-zero probability of being labeled with more than one fact type simultaneously; for example, "kidney failure" could be labeled as representing both a Body Site and a Problem. In some embodiments, classifiers may be trained to identify sub-portions of an entity label. For example, the feature "-itis" could have a probability $p_B$ of its token being at the beginning of a "Problem" entity label, a probability $p_I$ of its token being inside a "Problem" entity label (but not at the beginning of the label), and a probability $p_O$ of its token being outside a "Problem" entity label (i.e., of its token not being part of a "Problem" entity).

In some embodiments, the statistical entity detection model may be further trained to weight the individual features of a token to determine an overall probability that it should be associated with a particular entity label. For example, if the token "sinusitis" has n extracted features f1 . . . fn having respective probabilities p1 . . . pn of being associated with a "Problem" entity label, the statistical model may be trained to apply respective weights w1 . . . wn to the feature probabilities, and then combine the weighted feature probabilities in any suitable way to determine the overall probability that "sinusitis" should be part of a "Problem" entity. Any suitable technique for determining such weights may be used, including known modeling techniques such as maximum entropy modeling, support vector machines, conditional random fields, and/or others, as aspects of the invention are not limited in this respect.

In some embodiments, when an unlabeled text is input to the trained statistical entity detection model, the model may process the text to extract features and determine probabilities for individual tokens of being associated with various entity (e.g., fact type) labels. In some embodiments, the most probable label (including the non-entity label, if it is most probable) may be selected for each token in the input text. In other embodiments, labels may be selected through more contextual analysis, such as at the phrase level or sentence level, rather than at the token level. Any suitable technique, such as Viterbi techniques, or any other suitable technique, may be used, as aspects of the invention are not limited in this respect. In some embodiments, a lattice may be constructed of the associated probabilities for all entity types for all tokens in a sentence, and the best (e.g., highest combined probability) path through the lattice may be selected to determine which word sequences in the sentence are to be automatically labeled with which entity (e.g., fact type) labels. In some embodiments, not only the best path may be identified, but also the (N−1)-best alternative paths with the next highest associated probabilities. In some embodiments, this may result in an N-best list of alternative hypotheses for fact type labels to be associated with the same input text.

In some embodiments, a statistical model may also be trained to associate fact types extracted from new reports with particular facts to be extracted from those reports (e.g., to determine a particular concept represented by the text portion that has been labeled as an entity mention). For example, in some embodiments, a statistical fact extraction model may be applied to automatically label "acute sinusitis" not only with the "Problem" entity (fact type) label, but also with a label indicating the particular medical fact (e.g., concept) indicated by the word sequence (e.g., the medical fact "sinusitis, acute"). In such embodiments, for example, a single statistical model may be trained to detect specific particular facts as individual entities. For example, in some embodiments, the corpus of training text may be manually labeled by one or more human annotators with labels indicating specific medical facts, rather than labels indicating more general entities such as fact types or categories. However, in other embodiments, the process of detecting fact types as entities may be separated from the process of relating detected fact types to particular facts. For example, in some embodiments, a separate statistical model (e.g., an entity detection model) may be trained to automatically label portions of text with fact type labels, and another separate statistical model (e.g., a relation model) may be trained to identify which labeled entity (fact type) mentions together indicate a single specific medical fact. In some cases, the relation model may identify particular medical facts by relating together two or more mentions labeled with the same entity type.

For example, in the text, "Patient is complaining of acute sinusitis," in some embodiments an entity detection model may label the tokens "acute" and "sinusitis" as being part of a "Problem" entity. In some embodiments, a relation model, given that "acute" and "sinusitis" have been labeled as "Problem," may then relate the two tokens together to a single medical fact of "sinusitis, acute." For another example, consider the text, "Patient has sinusitis, which appears to be chronic." In some embodiments, an entity detection model may be applied to label the tokens "sinusitis" and "chronic" as "Problem" entity mentions. In some embodiments, a relation model may then be applied to determine that the two "Problem" entity mentions "sinusitis" and "chronic" are related (even though they are not contiguous in the text) to represent a single medical fact of "sinusitis, chronic." For yet another example, consider the text, "She has acute sinusitis; chronic attacks of asthma may be a factor." In some embodiments, an entity detection model may label each of the tokens "acute," "sinusitis," "chronic," and "asthma" as belonging to "Problem" entity mentions. In some embodiments, a relation model may then be applied to determine which mentions relate to the same medical fact. For example, the relation model may determine that the tokens "acute" and "sinusitis" relate to a first medical fact (e.g., "sinusitis, acute"), while the tokens "chronic" and "asthma" relate to a different medical fact (e.g., "asthma, chronic"), even though the token "chronic" is closer in the sentence to the token "sinusitis" than to the token "asthma."

In some embodiments, a relation model may be trained statistically using methods similar to those described above for training the statistical entity detection model. For example, in some embodiments, training texts may be manually labeled with various types of relations between entity mentions and/or tokens within entity mentions. For example, in the training text, "Patient has sinusitis, which appears to be chronic," a human annotator may label the "Problem" mention "chronic" as having a relation to the "Problem" mention "sinusitis," since both mentions refer to the same medical fact. In some embodiments, the relation annotations may simply indicate that certain mentions are related to each other, without specifying any particular type of relationship. In other embodiments, relation annotations may also indicate specific types of relations between entity mentions. Any suitable number and/or types of relation annotations may be used, as aspects of the invention are not limited in this respect. For example, in some embodiments, one type of relation annotation may be a "split" relation label. The tokens "sinusitis" and "chronic," for example, may be labeled as having a split relationship, because "sinusitis" and "chronic" together make up an entity, even though they are not contiguous within the text. In this case, "sinusitis" and "chronic" together indicate a specific type of sinusitis fact, i.e., one that it is chronic and not, e.g., acute. Another exemplary type of relation may be an "attribute" relation. In some embodiments, one or more system developers may define sets of attributes for particular fact types, corresponding to related information that may be specified for a fact type. For example, a "Medication" fact type may have attributes "dosage," "route," "frequency," "duration," etc. In another example, an "Allergy" fact type may have attributes "allergen," "reaction," "severity," etc. It should be appreciated, however, that the foregoing are merely examples, and that aspects of the invention are not limited to any particular attributes for any particular fact types. Also, other types of fact relations are possible, including family relative relations, causes-problem relations, improves-problem relations, and many others. Aspects of the invention are not limited to use of any particular relation types.

In some embodiments, using techniques similar to those described above, the labeled training text may be used as input to train the statistical relation model by extracting features from the text, and probabilistically associating the extracted features with the manually supplied labels. Any suitable set of features may be used, as aspects of the invention are not limited in this respect. For example, in some embodiments, features used by a statistical relation model may include entity (e.g., fact type) labels, parts of speech, parser features, N-gram features, token window size (e.g., a count of the number of words or tokens present between two tokens that are being related to each other), and/or any other suitable features. It should be appreciated, however, that the foregoing features are merely exemplary, as embodiments are not limited to any particular list of features. In some embodiments, rather than outputting only the best (e.g., most probable) hypothesis for relations between entity mentions, a statistical relation model may output a list of multiple alternative hypotheses, e.g., with corresponding probabilities, of how the entity mentions labeled in the input text are related to each other. In yet other embodiments, a relation model may be hard-coded and/or otherwise rule-based, while the entity detection model used to label text portions with fact types may be trained statistically.

In some embodiments, the relation model or another statistical model may also be trained to track mentions of the same entity from different sentences and/or document sections and to relate them together. Exemplary techniques for entity tracking are described in the publication by Florian cited above.

In some embodiments, further processing may be applied to normalize particular facts extracted from the text to standard forms and/or codes in which they are to be documented. For example, medical personnel often have many different ways of phrasing the same medical fact, and a normalization/coding process in some embodiments may be applied to identify the standard form and/or code corresponding to each extracted medical fact that was stated in a non-standard way. The standard form and/or code may be derived from any suitable source, as aspects of the invention are not limited in this respect. Some standard terms and/or codes may be derived from a government or profession-wide standard, such as SNOMED (Systematized Nomenclature of Medicine), UMLS (Unified Medical Language System), RxNorm, RadLex, etc. Other standard terms and/or codes may be more locally derived, such as from standard practices of a particular locality or institution. Still other standard terms and/or codes may be specific to the documentation system including the fact extraction component being applied.

For example, given the input text, "His sinuses are constantly inflamed," in some embodiments, an entity detection model together with a relation model (or a single model performing both functions) may identify the tokens "sinuses," "constantly" and "inflamed" as representing a medical fact. In some embodiments, a normalization/coding process may then be applied to identify the standard form for documenting "constantly inflamed sinuses" as "sinusitis, chronic." Alternatively or additionally, in some embodiments the normalization/coding process may identify a standard code used to document the identified fact. For example, the ICD-9 code for "sinusitis, chronic" is ICD-9 code #473. Any suitable coding system may be used, as aspects of the invention are not limited in this respect. Exemplary standard codes include ICD (International Classification of Diseases) codes, CPT (Current Procedural Terminology) codes, E&M (Evaluation and Management) codes, MedDRA (Medical Dictionary for Regulatory Activities) codes, SNOMED codes, LOINC (Logical Observation Identifiers Names and Codes) codes, RxNorm codes, NDC (National Drug Code) codes and RadLex codes.

In some embodiments, a normalization/coding process may be rule-based (e.g., using lists of possible ways of phrasing particular medical facts, and/or using an ontology of medical terms and/or other language units to normalize facts extracted from input text to their standard forms). For example, in some embodiments, the tokens identified in the text as corresponding to a medical fact may be matched to corresponding terms in an ontology. In some embodiments, a list of closest matching terms may be generated, and may be ranked by their similarity to the tokens in the text. The similarity may be scored in any suitable way. For example, in one suitable technique, one or more tokens in the text may be considered as a vector of its component elements, such as words, and each of the terms in the ontology may also be considered as a vector of component elements such as words. Similarity scores between the tokens may then be computed by comparing the corresponding vectors, e.g., by calculating the angle between the vectors, or a related measurement such as the cosine of the angle. In some embodiments, one or more concepts that are linked in the ontology to one or more of the higher ranking terms (e.g., the terms most similar to the identified tokens in the text) may then be identified as hypotheses for the medical fact to be extracted from that portion of the text. Exemplary techniques that may be used in some embodiments are described in Salton, Wong & Yang: "A vector space model for automatic indexing," Communications of the ACM, November 1975. This publication is incorporated herein by reference in its entirety. However, these are merely examples, and any suitable technique(s) for normalizing entity tokens to standard terms may be utilized in some embodiments, as aspects of the invention are not limited in this respect.

In some embodiments, the normalization/coding process may output a single hypothesis for the standard form and/or code corresponding to each extracted fact. For example, the single output hypothesis may correspond to the concept linked in the ontology to the term that is most similar to the token(s) in the text from which the fact is extracted. However, in other embodiments, the normalization/coding process may output multiple alternative hypotheses, e.g., with corresponding probabilities, for the standard form and/or code corresponding to an individual extracted fact. Thus, it should be appreciated that in some embodiments multiple alternative hypotheses for a medical fact to be extracted from a portion of input text may be identified by fact extraction component 104. Such alternative hypotheses may be collected at any or all of various processing levels of fact extraction, including entity detection, entity relation, and/or normalization/coding stages. In some embodiments, the list of alternative hypotheses may be thresholded at any of the various levels, such that the final list output by fact extraction component 104 may represent the N-best alternative hypotheses for a particular medical fact to be extracted.

It should be appreciated that the foregoing are merely examples, and that fact extraction component 104 may be implemented in any suitable way and/or form, as aspects of the invention are not limited in this respect.

As discussed above, in some embodiments a statistical fact extraction model may use membership in one or more dictionaries as a feature for characterizing a token and determining whether it is part of a mention of an entity of interest. For example, the fact that the token "sinusitis" is a member of a dictionary of types of inflammation may make it more likely that "sinusitis" represents a "Problem" entity in the input text. Thus, in one example, when a set of features is being extracted for the token "sinusitis," a search may be conducted to determine whether "sinusitis" is a member of any relevant predefined dictionaries. When it is determined that "sinusitis" is a member of the "inflammation" dictionary, a "member of inflammation dictionary" feature may be included in the extracted set of features for the token "sinusitis." In general, a dictionary useful as a feature for a statistical model typically is a list of terms that fall under the common heading of the dictionary; usually, the terms listed in dictionary "X" are all "types of X." For example, the "inflammation" dictionary may consist of a list of terms for types of inflammation, such as "arthritis," "asthma," "celiac disease," "colitis," "fibromyalgia," "meningitis," "tendonitis," etc. In some embodiments, a statistical entity detection model may have learned a probability that tokens belonging to a particular dictionary are associated with a particular entity label. For example, the entity detection model may have learned that tokens in the "inflammation" dictionary have a probability $P_{problem}$ of being labeled as "Problem" entity mentions, based on the frequency with which tokens in the "inflammation" dictionary were hand-labeled as "Problem" entity mentions in the training corpus. When tasked with automatically labeling the input token "sinusitis," the statistical model may consider this probability associated with membership in the "inflammation" dictionary, together with other probabilities learned for other features of "sinusitis," and may combine the probabilities of all those features to determine a likelihood that "sinusitis" should be labeled as a "Problem" entity mention. In some cases, a token may be a member of more than one dictionary, and then more than one dictionary feature may be extracted for that token. For example, "sinusitis" could be a member of both an "inflammation" dictionary and a "respiratory system conditions" dictionary, and the statistical model may have learned for each of these dictionaries a different probability of corresponding to a "Problem" entity. In this example, both dictionary features may be extracted for the token "sinusitis," and the associated probabilities for both features may be considered (e.g., suitably weighted and combined) in evaluating the likelihood that "sinusitis" should be labeled as a "Problem" entity mention.

The inventors have recognized, however, that although dictionary membership may be a useful feature in entity detection and other statistical modeling techniques, accurate and complete predefined dictionaries are not often easy to come by, and often do not provide adequate coverage for many tokens that need to be labeled. For example, it could be useful to the entity detection task to know that "sinusitis" is a type of condition that occurs in an area of the head, but there may not be a dictionary available for "head-related conditions," or there may be a dictionary that includes some "head-related conditions" but is incomplete in that it does not include "sinusitis" for some reason. In such a situation, there may be no available feature that can be extracted for "sinusitis" to capture the knowledge that it is a head-related condition. Additionally, the inventors have also recognized that some predefined dictionaries may be overinclusive, in that one or more of their members do not actually belong in the categorization defined by the dictionary, when the token is considered in the classification task at hand. For example, the inventors have noted that the medical term "truncus arteriosus" appears in a publicly available dictionary of "body sites," but usually is used by physicians to denote a disorder, and not a body site, when documenting a patient encounter. (This is because the truncus arteriosus, when present in the heart, is a congenital defect.) The predefined dictionary of "body sites" may thus be detrimental to use as a feature for the token "truncus arteriosus" when it appears in a physician's report, since the dictionary feature may bias the statistical model toward labeling the token as a "Body Site," when it actually should be labeled as a "Disorder" or "Problem."

One possible solution to the above-recognized difficulties arising from reliance on dictionary features may be to manually construct task-specific dictionaries for every different type of entity detection task that may arise. However, the inventors have appreciated that such a process would be time-consuming and often impractical, would likely require a significant amount of expert knowledge and foresight as to exactly what terms would be encountered in input texts and exactly how they should be classified, and as such might defeat many of the advantages of employing statistical machine learning techniques as opposed to solely hand-coded rule-based models. Accordingly, the inventors have developed alternative techniques to replace or supplement the use of dictionary features in statistical entity detection and fact extraction. These alternative techniques may make use of knowledge, related to the classification of terms and/or their relationships with other known concepts, that is not easily reflected in pre-constructed dictionaries.

In some embodiments, one or more ontologies may be used to access multiple levels of known classifications of concepts relevant to terms in an input text, and/or to access other known relationships between relevant concepts that can aid in the fact extraction process. As used herein, the term "ontology" refers to any knowledge representation (which may be encoded and/or stored in any suitable data format) that includes representations of known concepts and of known relationships between those concepts. An ontology is often represented graphically as a set of nodes connected to each other by edges, with each node representing a concept and each edge connecting two nodes representing a relationship between the concepts represented by those two nodes. Any concept about which there is human knowledge can be represented as a node in an ontology, and any type of known relationship between concepts can be represented as an edge in an ontology. One type of concept relationship is a parent-child relationship (also referred to herein as a hypernym-hyponym relationship, or an "is-a" relationship), but other types of concept relationships may also be represented in ontologies, as discussed further below. A particular ontology may include multiple types of concept relationships. However, some particular types of ontologies may be more restricted, e.g., to only one type or certain types of concept relationships. For example, one particular type of ontology is a taxonomy, which includes only parent-child relationships. Any type of ontology (including, for example, a taxonomy) may be used with techniques described herein, as aspects of the invention are not limited to the use of any particular type of ontology.

Figure 5:
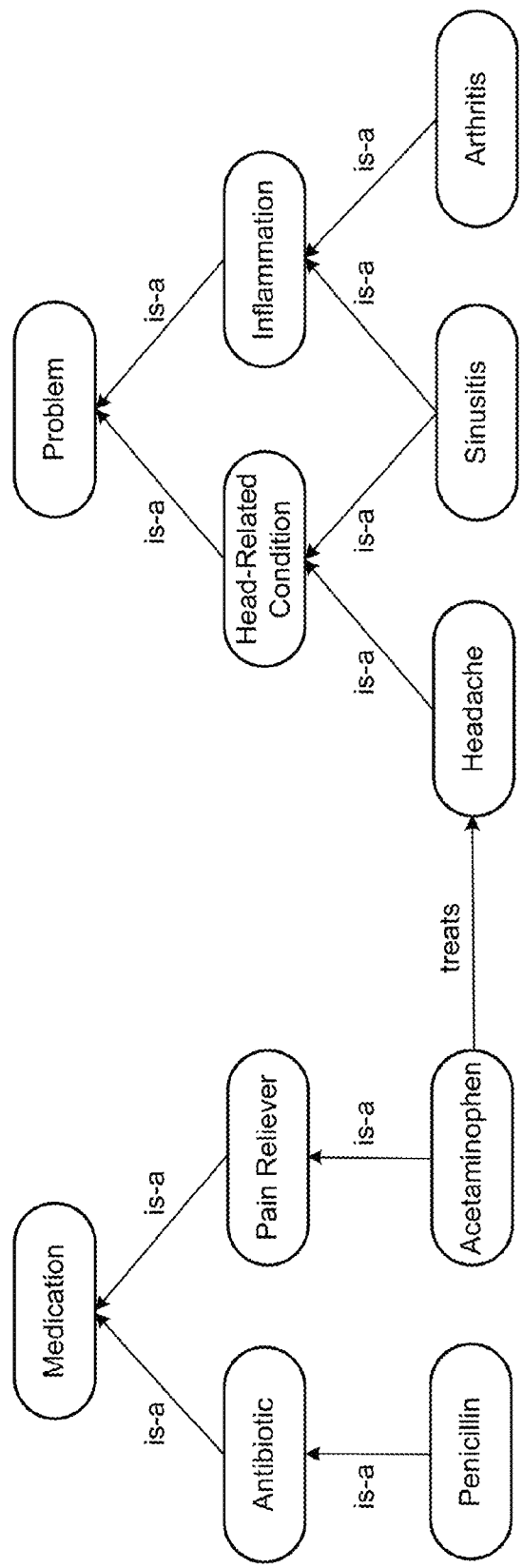
FIG. 5 illustrates a simple exemplary ontology that may be used in accordance with some embodiments of the present invention.

For illustration, FIG. 5 demonstrates an example of a simple (and non-comprehensive) ontology of a few medical concepts. Each ovoid shape in FIG. 5 graphically represents a node of the ontology, corresponding to a particular concept. The text inside a node is the tag assigned to the corresponding concept. For example, the node tagged "Medication" represents the concept of medication, about which humans have knowledge, such as characteristics of medications, and relationships between medication and other concepts within human knowledge. It should be appreciated, however, that the tag "Medication" is not the same as the concept itself. The concept of medication may be called different things by different people in different contexts (e.g., "medicine," "medicament," "drug," "treatment," etc.), and as such the concept of medication is not completely encapsulated by any single word. As used herein, different words or phrases that may be used in speech or text to refer to the same concept are referred to as different "terms" corresponding to the same concept. The concept may represent a semantic meaning that can be expressed in different ways by the different terms. As such, in some embodiments, one or more nodes of an ontology may each be associated with a set of known terms that may be used to refer to the corresponding concept. In some cases, a single term may also correspond to more than one concept, as when a word or word sequence can be used to express more than one semantic meaning. However, when representing ontology concepts in a data structure, it can be helpful to assign a single primary tag to each node, so that the node and its corresponding concept can be referred to and identified from among other nodes and corresponding concepts. In the example data structure of FIG. 5, a particular concept node has been tagged "Medication" for convenience; however, it could equivalently have been tagged with a different suitable designation (e.g., a "node ID"), such as a textual designation, a non-text designation such as a number, or some combination of text and non-text designations, unique to that ontology node and its corresponding concept.

Each arrow in FIG. 5 graphically represents an edge in the example ontology, corresponding to a particular relationship between the concepts corresponding to the two nodes connected by the arrow. Any type of concept relationship can be represented in an ontology, e.g., by marking the corresponding edge with a tag representing the type of relationship. For example, in FIG. 5, the "Antibiotic" node is connected to the "Medication" node by an arrow tagged "is-a," which represents a parent-child relationship between the concept of medication and the concept of antibiotic. As discussed above, a parent-child relationship denotes that the parent concept is a hypernym of the child concept, or equivalently that the child concept is a type of the parent concept. In this case, the "is-a" arrow between "Antibiotic" and "Medication" represents the knowledge that the concept of antibiotic is a child of the concept of medication (and equivalently, that the concept of medication is a parent of the concept of antibiotic), and therefore that an antibiotic is a type of medication. The graphical representation of the edge as an arrow indicates that the relationship is directional; i.e., an antibiotic is a type of medication, but medication is not a type of antibiotic. Although some concept relationships in an ontology may be directional (e.g., unidirectional), not all relationships need be. For example, an ontology could include a synonym relationship between the concepts "Dog" and "Canine," which would be bidirectional (or could potentially be described as nondirectional), to represent the knowledge that "Dog" is another word for "Canine," and "Canine" is also another word for "Dog."

Thus, the edges tagged "is-a" in the example ontology of FIG. 5 represent the following parent-child (also called "hypernym-hyponym") concept relationships:

An antibiotic is a type of medication.
Penicillin is a type of antibiotic.
A pain reliever is a type of medication.
Acetaminophen is a type of pain reliever.
A head-related condition is a type of Problem.
Headache is a type of head-related condition.

Sinusitis is a type of head-related condition.
Inflammation is a type of Problem.
Sinusitis is a type of inflammation.
Arthritis is a type of inflammation.

Transitive relationships can also be deduced by tracing connected paths of parent-child relationships within an ontology. For example, "Antibiotic" is a parent of "Penicillin," and "Medication" is a parent of "Antibiotic," which makes "Medication" a grandparent of "Penicillin" (and "Penicillin" a grandchild of "Medication"). These relationships represent the knowledge that penicillin is a type of antibiotic, and an antibiotic is a type of medication, therefore penicillin is a type of medication. These relationships (e.g., parent-child/hypernym-hyponym relationships) are said to be "hierarchical," since they establish a hierarchy in which parent concepts subsume their children concepts. As illustrated in FIG. 5, parts of an ontology (or an entire ontology) may be "strictly hierarchical," in which each concept node has at most one parent node. For example, the part of the ontology in FIG. 5 containing the nodes "Medication," "Antibiotic," "Pain Reliever," "Penicillin," and "Acetaminophen" is strictly hierarchical, because no concept node has more than one parent. In a strict hierarchy, any concept node may have any number of child nodes, as long as no node has more than one parent; thus, the fact that "Medication" has more than one child (i.e., "Antibiotic" and "Pain Reliever") does not destroy the strict hierarchy in this part of the ontology. In some embodiments, other parts of an ontology (or an entire ontology) may be "polyhierarchical," in which a concept node may have more than one parent node. For example, the part of the ontology in FIG. 5 containing the nodes "Head-Related Condition," "Inflammation," and "Sinusitis" is polyhierarchical, because "Sinusitis" has more than one parent (i.e., "Head-Related Condition" and "Inflammation").

When using an ontology, the description of certain hypernym-hyponym relationships as "parent-child" relationships allows for description of various other types of hierarchical relationships in a way that resembles a familiar family tree. For example, grandparent-grandchild relationships have already been described above. Parent-child and grandparent-grandchild relationships are examples of "ancestor-descendant" relationships, which can refer to direct relationships within a lineage that can traverse any number of connected parent-child relationships. For example, if "Penicillin" had a child node, that child node would be a descendant of "Medication," and "Medication" would be an ancestor of the child of "Penicillin." This ancestor-descendant relationship could also be described as a great-grandparent-great-grandchild relationship, since it traverses three parent-child relationships (i.e., three levels of hierarchy). However, for convenience, any ancestor-descendant relationship that traverses more than two levels of hierarchy (i.e., further removed than a grandparent-grandchild relationship) will simply be referred to herein as an "ancestor-descendant" relationship for convenience. Other familial names can be given to other types of hierarchically-related concepts in an ontology as well. For instance, in the example of FIG. 5, "Antibiotic" and "Pain Reliever" can be referred to as "sibling" concepts, since they share the same parent concept ("Medication"). Similarly, "Penicillin" and "Acetaminophen" can be referred to as "cousin" concepts, since they share the same grandparent concept ("Medication"), but not the same parent concept.

In some ontologies, not every concept relationship need be hierarchical. For example, in FIG. 5, the relationship between "Acetaminophen" and "Headache" is not hierarchical, as acetaminophen is not a type of headache, and headache is not a type of acetaminophen. Rather, the relationship between "Acetaminophen" and "Headache" is represented by an edge tagged "treats," which represents a different type of relationship than the "is-a" tag for parent-child relationships. In this example, the "treats" relationship represents the relationship between a medication and a medical problem that the medication can be used to treat. The "treats" relationship between "Acetaminophen" and "Headache" represents the knowledge that the medication acetaminophen can be used to treat the medical problem of headache. Although the arrow denotes that this particular relationship is directional (acetaminophen treats headache; headache does not treat acetaminophen), it is not hierarchical, as explained above. In the example of FIG. 5, the non-hierarchical nature of the "treats" relationship is signified by the fact that the arrow is horizontal rather than vertical.

When used in computer-implemented technology, an ontology may be represented as computer-readable data in any suitable format. For example, in some embodiments, a data representation of an ontology may include a list or table of the concept nodes in the ontology. In some embodiments, each concept node may be designated by a unique node ID (e.g., a number, an alphanumeric sequence or code, or any other suitable form of identifier) included in the list or table. For example, the concepts of the example ontology of FIG. 5 could be represented in a data structure including a table such as the following:

| Node ID | Tag |
| --- | --- |
| 01 | Medication |
| 02 | Problem |
| 03 | Antibiotic |
| 04 | Pain Reliever |
| 05 | Head-Related Condition |
| 06 | Inflammation |
| 07 | Penicillin |
| 08 | Acetaminophen |
| 09 | Headache |
| 10 | Sinusitis |
| 11 | Arthritis |

In some embodiments, the table of concept nodes may include a further column that lists, for each node ID, the known set of terms that may be used to refer to the corresponding concept. For example, this column might include, for node ID 01, the set of terms {"medication," "medicine," "medicament," "drug," "treatment"}; for node ID 08, the set of terms {"acetaminophen," "Tylenol," "Panadol"}; etc. The "Tag" and "Terms" columns are not required, however, and any other suitable columns may be included alternatively or additionally, as aspects of the invention are not limited to the use of ontologies stored in any particular data format.

In some embodiments, a data representation of an ontology may include a table or other type of listing of the concept relationships in the ontology. For example, such a table could include a row for each concept relationship, with the type of relationship and the concept node IDs involved in the relationship listed in the appropriate row. The directionality of a relationship could be explicitly listed in the appropriate row, or could be implied from the order in which the node IDs involved are listed. Any other suitable columns could be included as well, such as the tags for the corresponding node IDs, and/or any other suitable columns, as aspects of the invention are not limited to the use of ontologies stored in any particular data format. For example, a table of concept relationships could be constructed for the example ontology of FIG. 5 as follows:

| Node ID 1 | Relationship Type | Node ID 2 |
|---|---|---|
| 03 | is-a | 01 |
| 04 | is-a | 01 |
| 05 | is-a | 02 |
| 06 | is-a | 02 |
| 07 | is-a | 03 |
| 08 | is-a | 04 |
| 08 | treats | 09 |
| 09 | is-a | 05 |
| 10 | is-a | 05 |
| 10 | is-a | 06 |
| 11 | is-a | 06 |

Such a data structure for encoding the information contained in an ontology could be stored in the form of a relational database, or in any other suitable data format. However, it should be appreciated that the foregoing description is provided by way of example only, as aspects of the invention are not limited to the use of ontologies represented, encoded and/or stored in any particular data format.

Figure 6A:
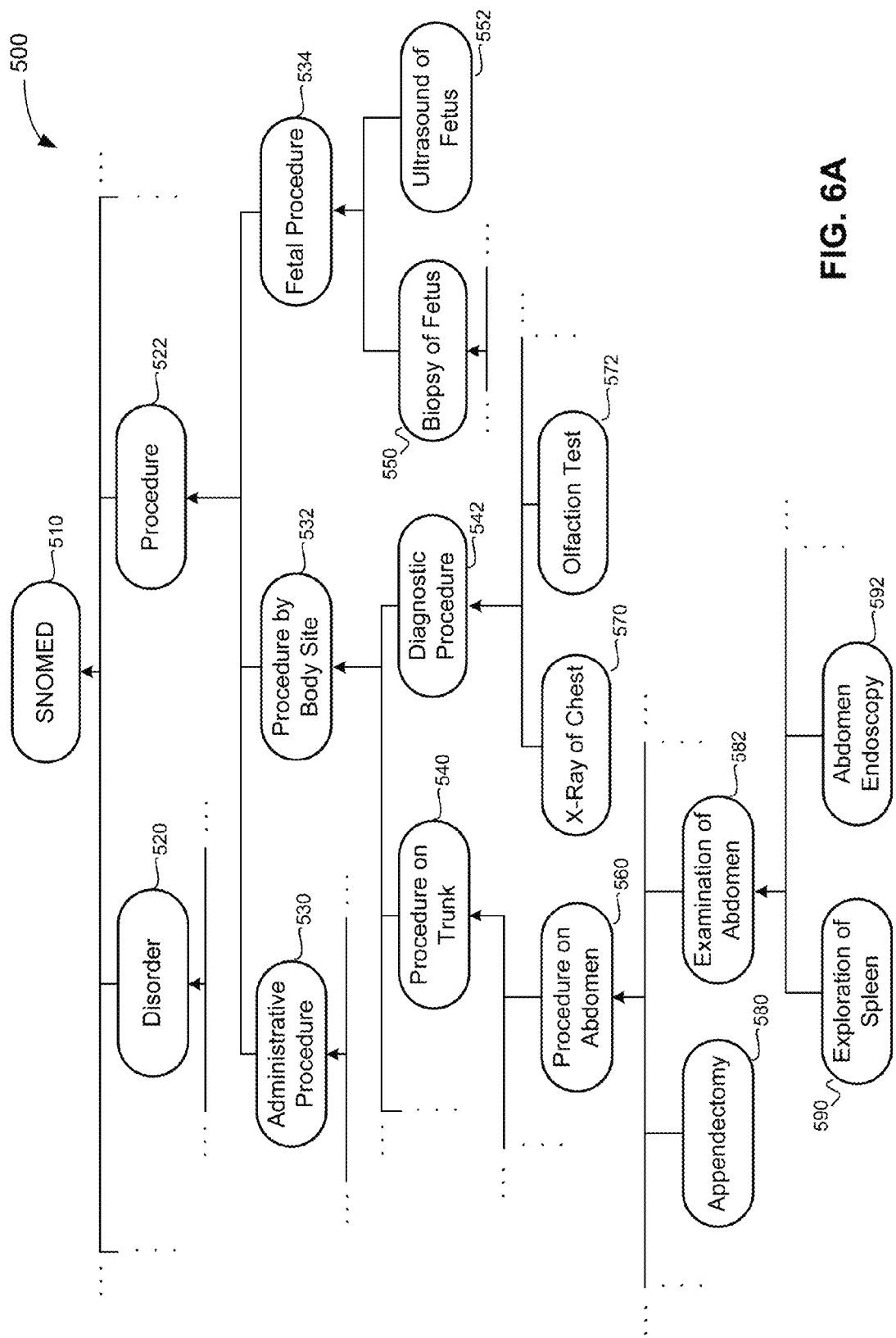
FIGS. 6A and 6B illustrate a more complex exemplary ontology that may be used in accordance with some embodiments of the present invention.

Shown in FIG. 6A is another example ontology, a portion of the SNOMED ontology promulgated by the International Health Terminology Standards Development Organisation. Each ovoid shape in FIG. 6A graphically represents a node in the ontology, corresponding to a medical concept. Node 510 is the root node representing the ontology itself, and is a parent/ancestor of all other nodes in the ontology. Other nodes in the ontology represent specific concepts, and are each tagged with one possible term or other suitable tag for the corresponding medical concept. An individual node within the ontology may have a set of one or more corresponding terms associated with the node ID in an appropriate data structure. For example, node 550 is tagged "Biopsy of Fetus," but the corresponding concept may also have other corresponding terms, such as "fetoscopic biopsy," "fetal biopsy," "intrauterine biopsy," etc. For exemplary purposes, below is a list of alternative terms that may be stored for concept nodes depicted in FIG. 6A:

| Node ID | Tag | Terms |
|---|---|---|
| 550 | Biopsy of Fetus | fetoscopic biopsy<br>fetal biopsy<br>intrauterine biopsy |
| 552 | Ultrasound of Fetus | neonatal ultrasound<br>ultrasound of fetus<br>ultrasound |
| 570 | X-Ray of Chest | chest x-ray<br>x-ray of chest cavity |
| 572 | Olfaction Test | smell test<br>smell test by bottle |
| 560 | Procedure on Abdomen | abdominal surgery<br>surgery on abdomen |
| 580 | Appendectomy | appendectomy<br>removal of appendix |
| 582 | Examination of Abdomen | abdominal exploration surgery |
| 590 | Exploration of Spleen | exploration of spleen<br>spleen examination |
| 592 | Abdomen Endoscopy | abdominal endoscopy<br>endoscopy of abdomen |

As can be seen from this example, a concept's tag may or may not be included in the set of terms associated with that concept. In some cases, it may be convenient to apply to a particular concept a tag that is not typically used by clinicians as a term when speaking or writing about that concept. In such cases, the tag may not be included in the concept's associated set of terms. Additionally, some concept nodes in the ontology may not have more than one associated term, and some concept nodes may not have any associated terms. For example, some concept nodes (e.g., "Procedure by Body Site" node 532) may be included in the ontology mainly for organizational purposes, as parent nodes for other concepts in the ontology, although clinicians may not normally refer to those organizational concept nodes in medical reports. If a node corresponds to a concept that is not normally explicitly included in clinicians' reports, it may not have associated terms representing how it would typically be expressed in language.

Edges in the ontology of FIG. 6A are represented by branching lines connecting individual nodes. In this example ontology, all relationships are "is-a" (parent-child) relationships and are unidirectional, although for simplicity no arrowheads are shown. However, the restriction to parent-child relationships is not required; as discussed above, some embodiments may use one or more ontologies that include any suitable type(s) of relationships, as aspects of the invention are not limited in this respect. Nodes at each vertical level of FIG. 6A are parents of the connected node(s) at the next level down. Thus, the following parent-child (hypernym-hyponym) relationships within the SNOMED ontology are depicted in FIG. 6A:

| Child Node ID | Parent Node ID | Concepts and Relationship |
|---|---|---|
| 530 | 522 | Administrative Procedure is a Procedure. |
| 532 | 522 | Procedure by Body Site is a Procedure. |
| 540 | 532 | Procedure on Trunk is a Procedure by Body Site. |
| 560 | 540 | Procedure on Abdomen is a Procedure on Trunk. |
| 580 | 560 | Appendectomy is a Procedure on Abdomen. |
| 582 | 560 | Examination of Abdomen is a Procedure on Abdomen. |
| 590 | 582 | Exploration of Spleen is an Examination of Abdomen. |
| 592 | 582 | Abdomen Endoscopy is an Examination of Abdomen. |
| 542 | 532 | Diagnostic Procedure is a Procedure by Body Site. |
| 570 | 542 | X-Ray of Chest is a Diagnostic Procedure. |
| 572 | 542 | Olfaction Test is a Diagnostic Procedure. |
| 534 | 522 | Fetal Procedure is a Procedure. |
| 550 | 534 | Biopsy of Fetus is a Fetal Procedure. |
| 552 | 534 | Ultrasound of Fetus is a Fetal Procedure. |

Ellipses in FIG. 6A represent edges and nodes that exist in the publicly available SNOMED ontology but are omitted from FIG. 6A for ease of illustration. For example, the top level of the SNOMED ontology hierarchy contains more nodes other than "Disorder" node 520 and "Procedure" node 522, although they are not shown in FIG. 6A; "Disorder" node 520 has child nodes that are not depicted in FIG. 6A; "Administrative Procedure" node 530 has child nodes that are not depicted in FIG. 6A; etc.

As discussed above, the inventors have recognized that one or more ontologies with multiple levels of hypernym-hyponym hierarchy may be beneficially used in natural language understanding processes such as entity detection. Any suitable ontology may be used, as aspects of the invention are not limited in this respect. An ontology may be obtained from any suitable source, such as a preexisting publicly, privately or commercially available ontology, or may be constructed specifically for the entity detection task and/or related tasks. Examples of suitable ontologies in the medical domain include SNOMED-CT, RxNorm, ICD-9, and MEDCIN (maintained by Medicomp Systems). The ontology in FIG. 6A is excerpted from the SNOMED ontology of medical concepts and terms, and may be useful in entity detection in the medical domain. However, it should be appreciated that aspects of the invention are not limited to the use of any particular ontology or any particular domain. The inventors have recognized that techniques described herein may be particularly applicable to medical domains since pre-constructed ontologies may be readily available for medical domains. However, it should be appreciated that the techniques described herein may utilize other ontologies and may be applied to any suitable entity detection task in any suitable domain, including domains other than medicine.

The inventors have appreciated that knowledge of the hierarchical classifications and other relationships between concepts in an ontology may provide useful information that can improve the accuracy of entity detection and labeling. For instance, consider the example in which a clinician's report states that a "spleen examination" was performed on a patient, and the entity detection model is tasked with determining whether the token "spleen examination" should be labeled as an "invasive medical procedure" entity (i.e., a procedure requiring incision or insertion of surgical implements into the patient's body). Suppose that in the corpus used to train the statistical entity detection model, the token "spleen examination" appeared rarely or not at all. In this case, the model may not have reliable information with which to determine an entity label for "spleen examination" based on the token itself, and it may be beneficial to look to other sources of information to determine a reliable probability with which the "invasive medical procedure" entity label may apply to the "spleen examination" token. The inventors have recognized that the hierarchical relationships in an ontology such as that of FIG. 6A may be useful for providing such information. From the ontology data structure, it can be determined that "spleen examination" is a term corresponding to concept node 590 tagged "Exploration of Spleen," and the hierarchical relationships between concept 590 and other concept nodes in the ontology can be traced. At a first level of hierarchy, it can be determined from the ontology that "Exploration of Spleen" is a type of "Examination of Abdomen;" at the next level of hierarchy, it can be determined that "Examination of Abdomen" (which subsumes "Exploration of Spleen") is a type of "Procedure on Abdomen;" and so on. In determining whether a "spleen examination" is likely an "invasive medical procedure," then, it may be useful to investigate whether an "Examination of Abdomen" is likely an "invasive medical procedure," whether a "Procedure on Abdomen" is likely an "invasive medical procedure," and so on.

The inventors have recognized that such information may be collected and utilized by including, in the set of entity detection features for a token in a text being analyzed, other concepts that are related in an ontology to the concept that matches that token. As discussed above, a statistical entity detection model may be configured to extract a number of features to be used in labeling a token. In some embodiments, concepts that are hierarchically related in an ontology to the concept matching the token to be labeled may be included in that token's feature set. In some embodiments, a concept in an ontology may be identified as matching a token in a text being analyzed when the token is one of the terms or tags corresponding to the concept, or when the token can be normalized to one of the terms or tags of the matching concept. Thus, in the example of FIG. 6A, "spleen examination" is one of the terms corresponding to "Exploration of Spleen" node 590, and thus the "Exploration of Spleen" concept 590 is the matching concept for the token "spleen examination." An exemplary set of features for the token "spleen examination" may include the following:

Feature:

| | |
|---|---|
| Token: | "spleen examination" |
| Part of Speech: | noun |
| Affix: | -tion |
| Matching Concept: | 590 ("Exploration of Spleen") |
| Parent Concept: (Ancestor Concept 1) | 582 ("Examination of Abdomen") |
| Grandparent Concept: (Ancestor Concept 2) | 560 ("Procedure on Abdomen") |
| Ancestor Concept 3: | 540 ("Procedure on Trunk") |
| Ancestor Concept 4: | 532 ("Procedure by Body Site") |
| Ancestor Concept 5: | 522 ("Procedure") |

In this example, the matching concept and all of its ancestor (hypernym) concepts are included as features of the token being processed by the entity detection model. However, aspects of the invention are not limited to this example, and other sets of concepts may alternatively be defined for inclusion in the feature set. For example, in some embodiments, descendant (hyponym) concepts of the matching concept, if any, may alternatively or additionally be included in the feature set. In some embodiments, concepts that are hierarchically (strictly hierarchically or polyhierarchically) related to the matching concept in ways other than as direct ancestors or descendants may be included. In one example, other hierarchically related concepts such as sibling "Abdomen Endoscopy" concept 592, and/or parent's sibling "Appendectomy" concept 580, and/or a cousin concept such as a child of "Appendectomy," etc., may be included. In further embodiments, concepts that are related to the matching concept in ways other than hierarchically (e.g., like the "treats" relationship described above) may alternatively or additionally be included. The discussion that follows focuses on concepts that are related hierarchically as hypernyms of the matching concept; however, it should be appreciated that aspects of the invention are not so limited. Furthermore, in some cases, a token may be matched to more than one matching concept in an ontology. For example, the token "spleen examination" could be matched to concepts "Spleen" and "Examination," in addition to "Exploration of Spleen." In such cases, any suitable criteria may be used to determine which concepts to include as features of the token. For example, concepts related hierarchically to all of the matching concepts may be included as features of the token; or concepts related hierarchically to only one or a subset of the matching concepts may be included.

In some embodiments, to collect information pertaining to the likelihood that certain hypernym concepts correspond to certain entity type labels, those hypernym concepts may be included in the feature sets for tokens in the entity detection model's training corpus. Continuing with the example of FIG. 6A, when the token "abdominal endoscopy" is encountered in the training corpus, the features extracted for that token may include the following:

Feature:

| | |
|---|---|
| Token: | "abdominal endoscopy" |
| Matching Concept: | 592 ("Abdomen Endoscopy") |
| Parent Concept: | 582 ("Examination of Abdomen") |
| Grandparent Concept: | 560 ("Procedure on Abdomen") |
| Ancestor Concept 3: | 540 ("Procedure on Trunk") |

| Feature: | |
|---|---|
| Ancestor Concept 4: | 532 ("Procedure by Body Site") |
| Ancestor Concept 5: | 522 ("Procedure") |

If this instance of the token "abdominal endoscopy" in the training corpus is hand-labeled as an "invasive medical procedure" entity, then that may count as one instance in which each of concept nodes 522, 532, 540, 560, 582 and 592 were features of a token labeled "invasive medical procedure." The number of such instances throughout the entire training corpus may then be counted. For each node in the ontology, the number of tokens in the training corpus that are labeled "invasive medical procedure" and that have the respective concept node as a feature (either as a matching node or an ancestor node) may be counted. In some embodiments, this count may be compared with the total count of tokens in the training corpus that have the respective concept node as a feature (whether labeled "invasive medical procedure" or not) to determine a frequency or probability with which that concept node is associated with the "invasive medical procedure" entity type label. Thus, for example, "Examination of Abdomen" node 582 may be associated with the "invasive medical procedure" entity type label whenever "Exploration of Spleen" node 590 or "Abdomen Endoscopy" node 592 is associated with the entity type label; "Procedure on Abdomen" node 560 may be associated with the entity type label whenever "Appendectomy" node 580, "Examination of Abdomen" node 582, "Exploration of Spleen" node 590 or "Abdomen Endoscopy" node 592 is associated with the entity type label; and so on.

Figure 6B:
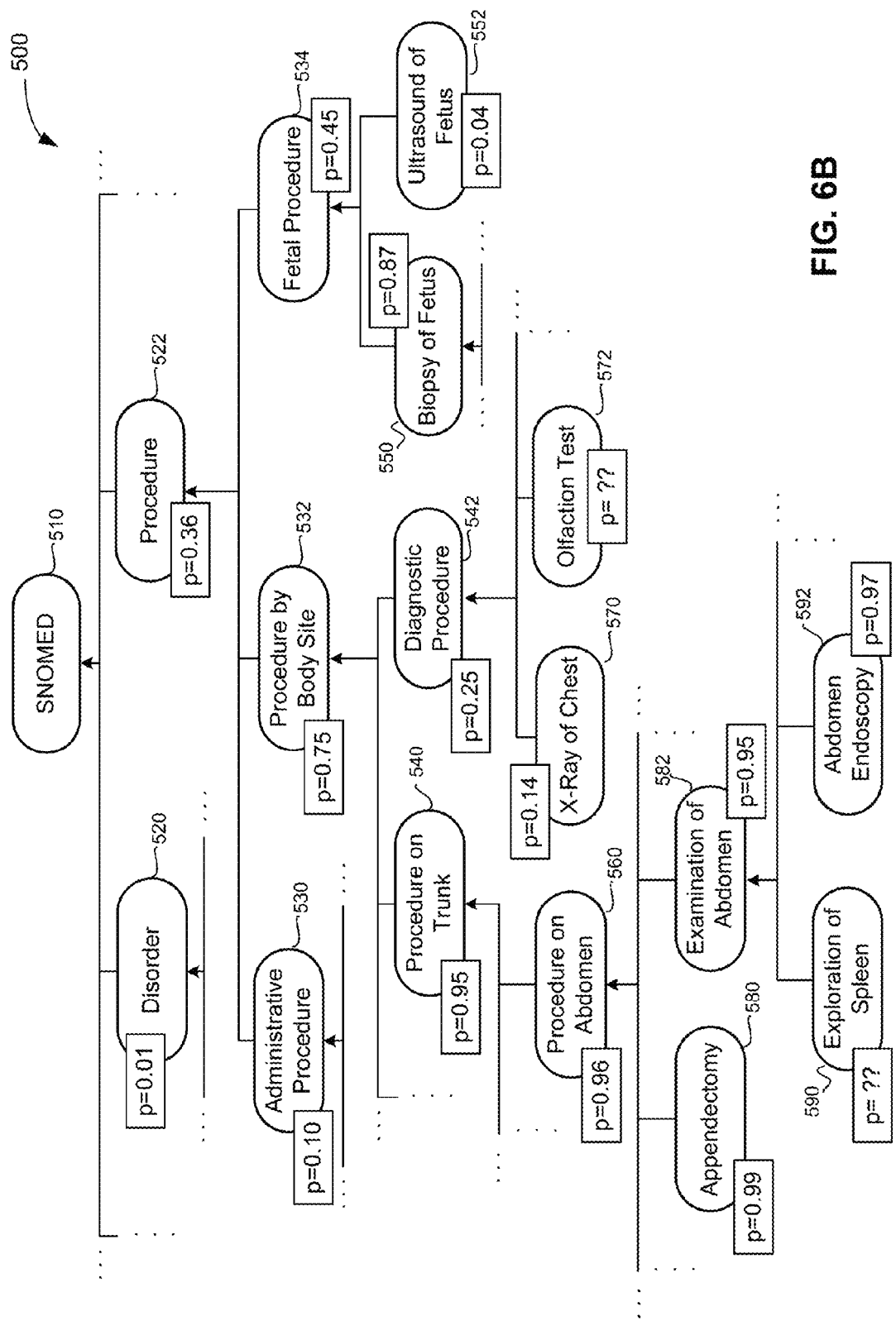

FIG. 6B depicts an example of the ontology portion of FIG. 6A after processing a training corpus to determine the probability of each concept node being a feature of a token labeled with the "invasive medical procedure" entity type label. As discussed above, in this example a concept node may be a feature of a token if the token matches the concept node (e.g., if the token is a term corresponding to the concept node), or if the concept node is an ancestor (hypernym) of the token's matching concept. Thus, for instance, in this example it has been determined that "Examination of Abdomen" node 582 has a probability 0.95 of being associated with the "invasive medical procedure" entity type label. That means that 95% of the tokens in the training corpus that matched concept node 582 or any of its descendant nodes (i.e., concept nodes 590, 592, etc.) were labeled as "invasive medical procedure" entities. Likewise, 96% of the tokens in the training corpus that matched "Procedure on Abdomen" concept node 560 or any of its descendant nodes (i.e., concept nodes 580, 582, 590, 592, etc.) were labeled as "invasive medical procedure" entities.

In some embodiments, known terms corresponding to concepts in an ontology may be pre-processed to determine their ontological features (related concept nodes) and corresponding probabilities, such that the ontology itself need not be stored in memory. A term's matching concept, related concepts (which may be all or a subset of the related concepts in the entire ontology), and the probabilities corresponding to those concepts may be stored, for example, in any suitable data structure, such as a look-up table, for use at run time in the entity detection process.

For some concept nodes (e.g., nodes 572 and 590) there may be no probability determined for the "invasive medical procedure" label, because no tokens matching those concept nodes (or any of their descendants, if any) appeared in the training corpus. This is different from a concept node having a zero probability for the "invasive medical procedure" label, which would indicate that one or more tokens matching the concept or its descendant(s) did appear in the training corpus, but were never labeled with the "invasive medical procedure" label. In some cases, a concept node may have an associated probability of being associated with a particular entity type label even though no tokens in the training corpus match that concept node itself. For example, "Procedure by Body Site" node 532 may not have any corresponding terms or matching tokens in the training corpus, but one or more of its descendant concepts may have matching tokens labeled "invasive medical procedure" with frequency/probability 0.75.

The inventors have thus recognized that use of ontological hypernym nodes as entity detection features as described herein may aid in improving statistical entity detection (e.g., when training data are sparse, or when input tokens are encountered whose matching concepts were not encountered in the training corpus). For example, when the token "spleen examination" is encountered in an input text, it may be difficult to determine, using conventional techniques, how likely the token is to correspond to an "invasive medical procedure" entity, since the token "spleen examination" was never encountered in the training corpus, nor were any other terms of the matching concept "Exploration of Spleen." However, by tracing the ancestry of the matching concept node 590 in the ontology of FIG. 6B, it can be seen that its parent concept "Examination of Abdomen" has a high likelihood (p=0.95) of corresponding to an "invasive medical procedure," and this may provide an indication that "spleen examination" may also be likely to correspond to an "invasive medical procedure." The known likelihood for the parent concept may have been determined from encountering one or more terms matching the parent concept in the training corpus, and/or from encountering others of the parent concept's descendants (e.g., the siblings of "Exploration of Spleen") in the training corpus. Thus, discriminative information for a concept never encountered in the training corpus may in some instances be inferred from the concept's relationships (e.g., hierarchical relationships) to other concepts in the ontology that were encountered in the training corpus.

In some embodiments, as discussed above, when an input text (e.g., a medical report from which medical facts are to be extracted) is processed by the statistical entity detection model, the model may extract a number of features from a token in the input text to determine whether to label the token with an entity type label. In some embodiments, ontological hypernyms may be included in the set of features extracted for the token under consideration. In the example of FIG. 6B, the features extracted for the token "spleen examination" may include the following features, along with their associated probabilities of corresponding to "invasive medical procedure" entities as determined from analysis of the training corpus (more or fewer features than listed below could also be used):

| Feature | | Probability |
|---|---|---|
| Token: | "spleen examination" | ?? |
| Part of Speech: | noun | 0.52 |
| Affix: | -tion | 0.61 |
| Matching Concept: | 590 ("Exploration of Spleen") | ?? |
| Hypernym Concept 1: | 582 ("Examination of Abdomen") | 0.95 |
| Hypernym Concept 2: | 560 ("Procedure on Abdomen") | 0.96 |
| Hypernym Concept 3: | 540 ("Procedure on Trunk") | 0.95 |
| Hypernym Concept 4: | 532 ("Procedure by Body Site") | 0.75 |
| Hypernym Concept 5: | 522 ("Procedure") | 0.36 |

In some embodiments, the extracted features for a token and their respective probabilities may be weighted and combined to determine a measure related to a likelihood (i.e., to determine the likelihood or a related measure) that the token corresponds to a particular entity type. For example, if the above features for "spleen examination" were weighted equally and averaged, the result would be a probability of 0.73 that the token corresponds to the "invasive medical procedure" entity type. In some embodiments, this determined probability or other likelihood-related measure may be compared with a suitable threshold to determine whether to label the token as the entity type being considered. Any suitable threshold may be used, as aspects of the invention are not limited in this respect. In this example, if the threshold probability were, e.g., 0.5, the entity detection model would label "spleen examination" as an "invasive medical procedure" entity in response to the token's determined probability being above the corresponding threshold. In some embodiments, different thresholds may be used in different contexts, such as for different entity types, different feature sets, different sections of the text in which the token appears, and/or any other suitable criteria. In some embodiments, the determined probability that a token corresponds to a particular entity type may not be compared to a static threshold, but may instead be compared to other determined probabilities that the token corresponds to other entity types. For example, the "spleen examination" token may be labeled as an "invasive medical procedure" entity in response to the determined probability for "invasive medical procedure" being higher than the determined probabilities for other entity types (possibly including a non-entity type) for that token.

In some embodiments, the features may not be weighted equally; instead, any suitable weighting criteria may be applied. In some embodiments, ontological features may be weighted based on the closeness of their hierarchical relationships to the token's matching concept (e.g., based on the distance traversed in the ontology tree). For example, in some embodiments the "matching concept" feature may be weighted more heavily than the "hypernym concept 1" (parent concept) feature, which may be weighted more heavily than the "hypernym concept 2" (grandparent concept) feature, and so on. Any suitable technique for determining feature weights may be used, including known modeling techniques such as maximum entropy modeling, support vector machines, conditional random fields, and/or others, as aspects of the invention are not limited in this respect. Furthermore, in some embodiments, ontological features may be weighted with respect to other (e.g., non-ontological) features extracted in the entity detection process.

In some embodiments, not all hypernyms of the matching concept (or other related concepts) may be included as features of the token; instead, only a limited number of levels of hierarchy in the ontology may be traversed (e.g., only the closest N ancestors of the matching concept may be included as features). In some embodiments, the number of levels of hierarchy (e.g., the number of hypernyms) that are included as features may be constant. In other embodiments, a variable number of levels of hierarchy may be included, based on the level in the hierarchy at which hypernyms become less discriminative for the entity type being considered. In the example of FIG. 6B, of the hypernyms of node 590, nodes 582, 560 and 540 all have high probabilities (0.95 or above) of corresponding to the "invasive medical procedure" entity type, but the probability decreases considerably between node 540 and node 532, and even more between node 532 and node 522. This is because, for example, most children of node 540 correspond to the "invasive medical procedure" entity type with high probability; whereas node 532 has one child branch (node 540 and its descendants) with high probability of corresponding to "invasive medical procedure," as well as another child branch (node 542 and its descendants) with low probability of corresponding to "invasive medical procedure." Thus, concept node 540 is considerably more discriminative for "invasive medical procedure" than concept node 532 is. In one example, then, concept nodes 590, 582, 560 and 540 may be included as features of the "spleen examination" token, while concept nodes 532 and 522 may not be included. In another example, a lower discriminative threshold may be selected, such that concept nodes 590, 582, 560, 540 and 532 may be included and concept node 522 may not be included. It should be appreciated that any suitable discriminative threshold may be used, as aspects of the invention are not limited in this respect.

In some embodiments, the subset of a matching concept's hypernyms to be used as entity detection features may be selected by pruning less discriminative concept nodes using any suitable pruning technique. One example of a suitable pruning technique may be to prune concept nodes having feature weights lower than a suitably selected threshold. Another example may be to apply a known learning algorithm such as a maximum mutual information technique. However, aspects of the invention are not limited to any particular feature pruning technique, nor to the use of any feature pruning technique at all.

Thus, in some embodiments, when processing an input text (such as a medical report) for entity detection, a statistical entity detection model may extract ontological features as part of a token's feature set. The model may be configured to match the token to a matching concept in the ontology, and to trace through multiple levels of hierarchy in the ontology to identify other concepts hierarchically related to the matching concept. These concepts may be included as features in the token's feature set, which may be mapped to a likelihood (or a related measure) that a portion of the input text (which may be the token itself or may include the token) corresponds to a particular entity type. The model may use the determined likelihood (or related measure) to determine whether to label the text portion as corresponding to that entity type. As discussed above, in some embodiments this entity detection process may be performed as part of a process of extracting medical facts from a text narrative provided by a clinician.

In some embodiments, a user such as clinician 120 may monitor, control and/or otherwise interact with the fact extraction and/or fact review process through a user interface provided in connection with system 100. For example, in some embodiments, user interface 140 may be provided by fact review component 106, e.g., through execution (e.g., by one or more processors of system 100) of programming instructions incorporated in fact review component 106. One exemplary implementation of such a user interface is graphical user interface (GUI) 200, illustrated in FIG. 2. In some embodiments, when the user is clinician 120, GUI 200 may be presented via user interface 110. In some embodiments, a user may be a person other than a clinician; for example, another person such as coding specialist 150 may be presented with GUI 200 via user interface 140. However, it should be appreciated that "user," as used herein, refers to an end user of system 100, as opposed to a software and/or hardware developer of any component of system 100.

The user interface is not limited to a graphical user interface, as other ways of providing data from system 100 to users may be used. For example, in some embodiments, audio indicators may be transmitted from system 100 and conveyed to a user. It should be appreciated that any type of user interface may be provided in connection with fact extraction, fact review and/or other related processes, as aspects of the invention are not limited in this respect. While the exemplary embodiments illustrated in FIG. 1 involve data processing at system 100 and data communication between system 100 and user interfaces 110 and/or 140, it should be appreciated that in other embodiments any or all processing components of system 100 may instead be implemented locally at user interface 110 and/or user interface 140, as aspects of the invention are not limited to any particular distribution of local and/or remote processing capabilities.

Figure 2:
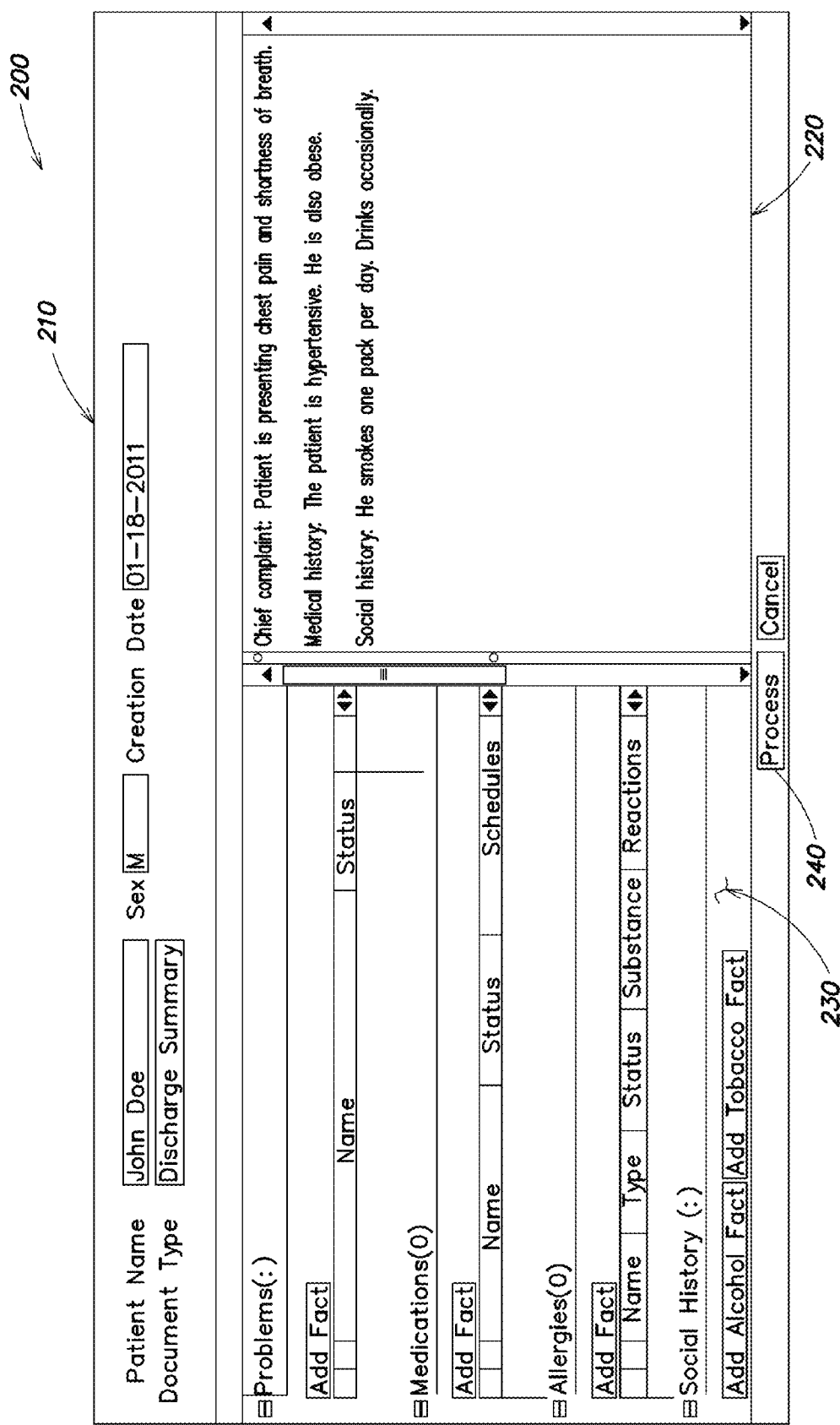
FIG. 2 is a screenshot illustrating an exemplary graphical user interface for a medical fact review system in accordance with some embodiments of the present invention.

As depicted in FIG. 2, GUI 200 includes a number of separate panes displaying different types of data. Identifying information pane 210 includes general information identifying patient 222 as a male patient named John Doe. Such general patient identifying information may be entered by clinician 120, or by other user 150, or may be automatically populated from an electronic medical record for patient 122, or may be obtained from any other suitable source. Identifying information pane 210 also displays the creation date and document type of the report currently being worked on. This information may also be obtained from any suitable source, such as from stored data or by manual entry. When referring herein to entry of data by clinician 120 and/or other user 150, it should be appreciated that any suitable form of data entry may be used, including input via mouse, keyboard, touch-screen, stylus, voice, or any other suitable input form, as aspects of the invention are not limited in this respect.

GUI 200 as depicted in FIG. 2 includes a text panel 220 in which a text narrative referring to the encounter between clinician 120 and patient 122 is displayed. In some embodiments, text panel 220 may include text editor functionality, such that clinician 120 may directly enter the text narrative into text panel 220, either during the patient encounter or at some time thereafter. If ASR is used to produce the text narrative from a spoken dictation provided by clinician 120, in some embodiments the text may be displayed in text panel 220 as it is produced by ASR engine 102, either in real time while clinician 120 is dictating, or with a larger processing delay. In other embodiments, the text narrative may be received as stored data from another source, such as from medical transcriptionist 130, and may be displayed in completed form in text panel 220. In some embodiments, the text narrative may then be edited if desired by clinician 120 and/or other user 150 within text panel 220. However, text editing capability is not required, and in some embodiments text panel 220 may simply display the text narrative without providing the ability to edit it.

Exemplary GUI 200 further includes a fact panel 230 in which one or more medical facts, once extracted from the text narrative and/or entered in another suitable way, may be displayed as discrete structured data items. When clinician 120 and/or other user 150 is ready to direct fact extraction component 104 to extract one or more medical facts from the text narrative, in some embodiments he or she may select process button 240 via any suitable selection input method. However, a user indication to begin fact extraction is not limited to a button such as process button 240, as any suitable way to make such an indication may be provided by GUI 200. In some embodiments, no user indication to begin fact extraction may be required, and fact extraction component 104 may begin a fact extraction process as soon as a requisite amount of text (e.g., enough text for fact extraction component 104 to identify one or more clinical facts that can be ascertained therefrom) is entered and/or received. In some embodiments, a user may select process button 240 to cause fact extraction to be performed before the text narrative is complete. For example, clinician 120 may dictate, enter via manual input and/or otherwise provide a part of the text narrative, select process button 240 to have one or more facts extracted from that part of the text narrative, and then continue to provide further part(s) of the text narrative. In another example, clinician 120 may provide all or part of the text narrative, select process button 240 and review the resulting extracted facts, edit the text narrative within text pane 220, and then select process button 240 again to review how the extracted facts may change.

Figure 3A:
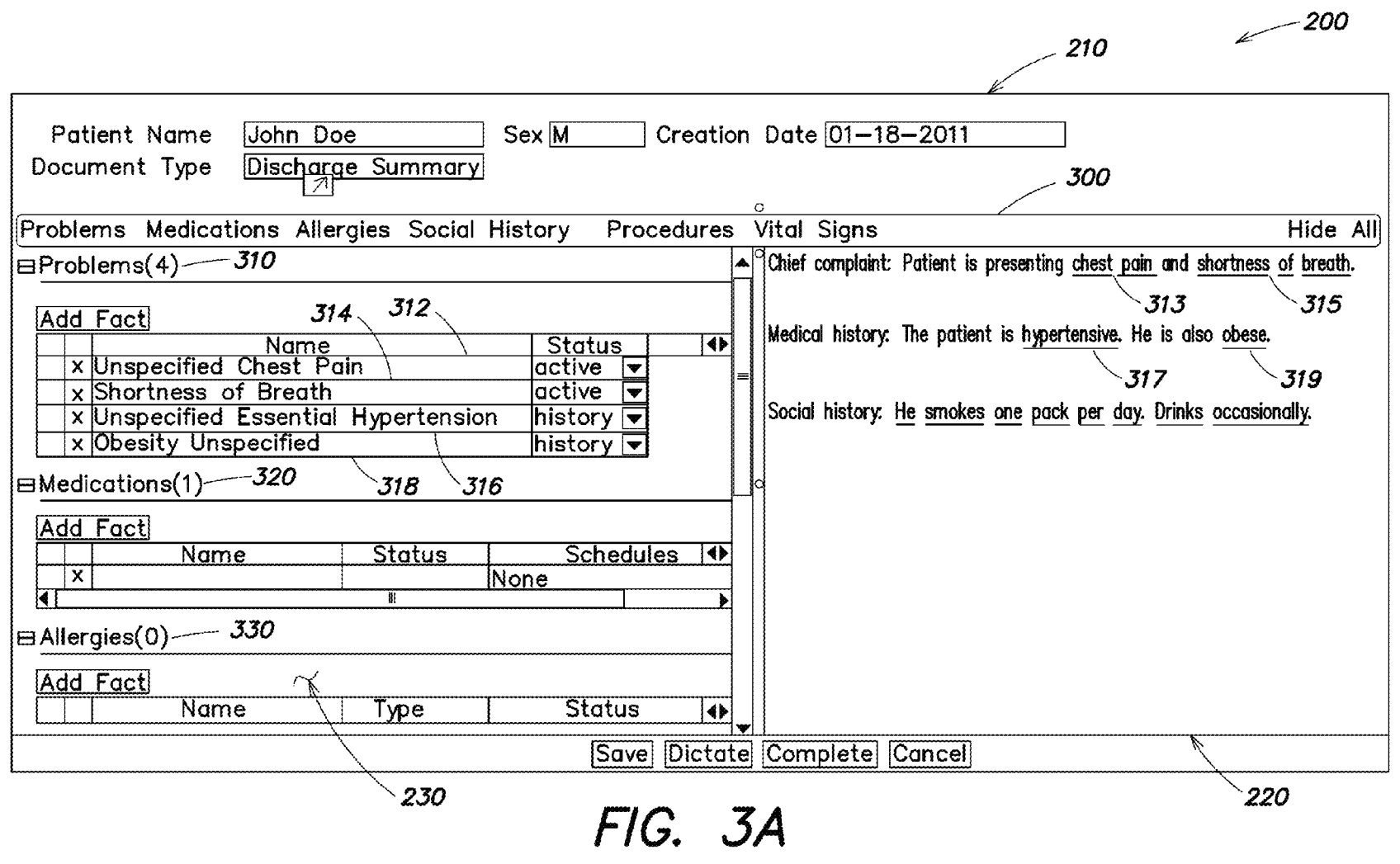
Figure 3B:
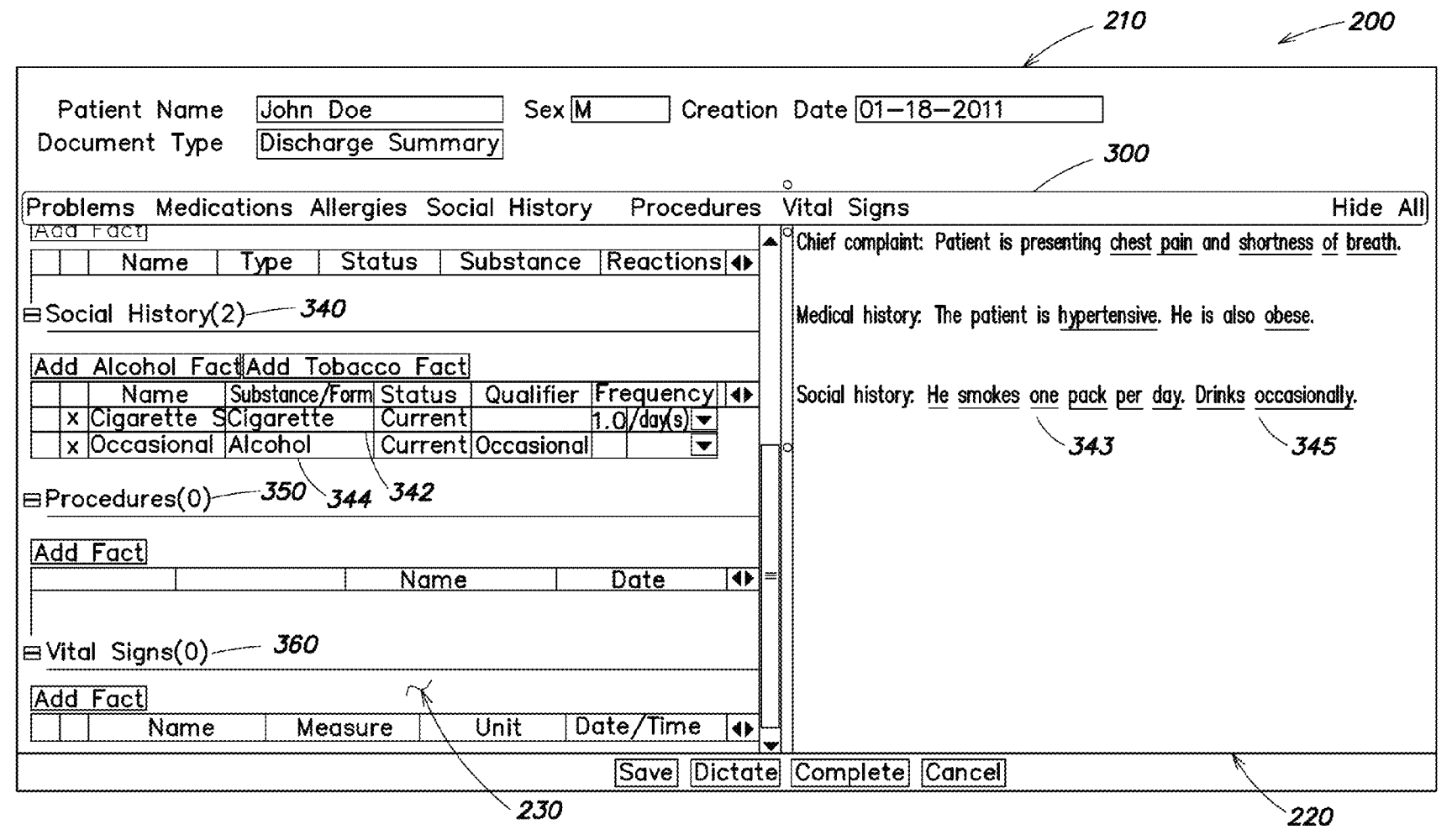

In some embodiments, one or more medical facts extracted from the text narrative by fact extraction component 104 may be displayed to the user via GUI 200 in fact panel 230. Screenshots illustrating an example display of medical facts extracted from an example text narrative are provided in FIGS. 3A and 3B. FIG. 3A is a screenshot with fact panel 230 scrolled to the top of a display listing medical facts extracted from the example text narrative, and FIG. 3B is a screenshot with fact panel 230 scrolled to the bottom of the display listing the extracted medical facts. In some embodiments, as depicted in FIGS. 3A and 3B, medical facts corresponding to a patient encounter may be displayed in fact panel 230, and organized into a number of separate categories of types of facts. An exemplary set of medical fact categories includes categories for problems, medications, allergies, social history, procedures and vital signs. However, it should be appreciated that any suitable fact categories may be used, as aspects of the invention are not limited in this respect. In addition, organization of facts into categories is not required, and displays without such organization are possible. As depicted in FIGS. 3A and 3B, in some embodiments GUI 200 may be configured to provide a navigation panel 300, with a selectable indication of each fact category available in the display of fact panel 230. In some embodiments, when the user selects one of the categories within navigation panel 300 (e.g., by clicking on it with a mouse, touchpad, stylus, or other input device), fact panel 230 may be scrolled to display the corresponding fact category. As depicted in FIGS. 3A and 3B, all available fact categories for the current document type are displayed, even if a particular fact category includes no extracted or otherwise entered medical facts. However, this is not required; in some embodiments, only those fact categories having facts ascertained from the patient encounter may be displayed in fact panel 230.

Fact panel 230 scrolled to the top of the display as depicted in FIG. 3A shows problem fact category 310, medications fact category 320, and allergies fact category 330. Within problem fact category 310, four medical facts have been extracted from the example text narrative; no medical facts have been extracted in medications fact category 320 or in allergies fact category 330. Within problem fact category 310, fact 312 indicates that patient 122 is currently presenting with unspecified chest pain; that the chest pain is a currently presenting condition is indicated by the status "active". Fact 314 indicates that patient 122 is currently presenting with shortness of breath. Fact 316 indicates that the patient has a history (status "history") of unspecified essential hypertension. Fact 318 indicates that the patient has a history of unspecified obesity. As illustrated in FIG. 3A, each medical fact in problem fact category 310 has a name field and a status field. In some embodiments, each field of a clinical fact may be a structured component of that fact represented as a discrete structured data item. In this example, the name field may be structured such that only a standard set of medical terms for problems may be available to populate that field. For example, the status field may be structured such that only statuses in the Systematized Nomenclature of Medicine (SNOMED) standard (e.g., "active" and "history") may be selected within that field, although other standards (or no standard) could be employed. An exemplary list of fact categories and their component fields is given below. However, it should be appreciated that this list is provided by way of example only, as aspects of the invention are not limited to any particular organizational system for facts, fact categories and/or fact components.

Exemplary List of Fact Categories and Component Fields

Category: Problems. Fields: Name, SNOMED status, ICD code.

Category: Medications. Fields: Name, Status, Dose form, Frequency, Measures, RxNorm code, Administration condition, Application duration, Dose route.

Category: Allergies. Fields: Allergen name, Type, Status, SNOMED code, Allergic reaction, Allergen RxNorm.

Category: Social history—Tobacco use. Fields: Name, Substance, Form, Status, Qualifier, Frequency, Duration, Quantity, Unit type, Duration measure, Occurrence, SNOMED code, Norm value, Value.

Category: Social history—Alcohol use. Fields: Name, Substance, Form, Status, Qualifier, Frequency, Duration, Quantity, Quantifier, Unit type, Duration measure, Occurrence, SNOMED code, Norm value, Value.

Category: Procedures. Fields: Name, Date, SNOMED code.

Category: Vital signs. Fields: Name, Measure, Unit, Unit type, Date/Time, SNOMED code, Norm value, Value.

In some embodiments, a linkage may be maintained between one or more medical facts extracted by fact extraction component 104 and the portion(s) of the text narrative from which they were extracted. As discussed above, such a portion of the text narrative may consist of a single word or may include multiple words, which may be in a contiguous sequence or may be separated from each other by one or more intervening words, sentence boundaries, section boundaries, or the like. For example, fact 312 indicating that patient 122 is currently presenting with unspecified chest pain may have been extracted by fact extraction component 104 from the words "chest pain" in the text narrative. The "active" status of extracted fact 312 may have been determined by fact extraction component 104 based on the appearance of the words "chest pain" in the section of the text narrative with the section heading "Chief complaint". In some embodiments, fact extraction component 104 and/or another processing component may be programmed to maintain (e.g., by storing appropriate data) a linkage between an extracted fact (e.g., fact 312) and the corresponding text portion (e.g., "chest pain").

In some embodiments, GUI 200 may be configured to provide visual indicators of the linkage between one or more facts displayed in fact panel 230 and the corresponding portion(s) of the text narrative in text panel 220 from which they were extracted. In the example depicted in FIG. 3A, the visual indicators are graphical indicators consisting of lines placed under the appropriate portions of the text narrative in text panel 220. Indicator 313 indicates the linkage between fact 312 and the words "chest pain" in the "Chief complaint" section of the text narrative; indicator 315 indicates the linkage between fact 314 and the words "shortness of breath" in the "Chief complaint" section of the text narrative; indicator 317 indicates the linkage between fact 316 and the word "hypertensive" in the "Medical history" section of the text narrative; and indicator 319 indicates the linkage between fact 318 and the word "obese" in the "Medical history" section of the text narrative. However, these are merely examples of one way in which visual indicators may be provided, as other types of visual indicators may be provided. For example, different or additional types of graphical indicators may be provided, and/or linked text in text panel 220 may be displayed in a distinctive textual style (e.g., font, size, color, formatting, etc.). Aspects of the invention are not limited to any particular type of linkage indicator.

In some embodiments, when the textual representation of the free-form narration provided by clinician 120 has been re-formatted and fact extraction has been performed with reference to the re-formatted version, the original version may nevertheless be displayed in text panel 220, and linkages may be maintained and/or displayed with respect to the original version. For example, in some embodiments, each extracted clinical fact may be extracted by fact extraction component 104 from a corresponding portion of the re-formatted text, but that portion of the re-formatted text may have a corresponding portion of the original text of which it is a formatted version. A linkage may therefore be maintained between that portion of the original text and the extracted fact, despite the fact actually having been extracted from the re-formatted text. In some embodiments, providing an indicator of the linkage between the extracted fact and the original text may allow clinician 120 and/or other user 150 to appreciate how the extracted fact is related to what was actually said in the free-form narration. However, other embodiments may maintain linkages between extracted facts and the re-formatted text, as an alternative or in addition to the linkages between the extracted facts and the original text, as aspects of the invention are not limited in this respect.

Fact panel 230 scrolled to the bottom of the display as depicted in FIG. 3B shows social history fact category 340, procedures fact category 350, and vital signs fact category 360. Within social history fact category 340, two medical facts have been extracted; no facts have been extracted in procedures fact category 350 and vital signs fact category 360. Within social history fact category 340, fact 342 indicates that patient 122 currently smokes cigarettes with a frequency of one pack per day. Fact 344 indicates that patient 122 currently occasionally drinks alcohol. Indicator 343 indicates that fact 342 was extracted from the words "He smokes one pack per day" in the "Social history" section of the text narrative; and indicator 345 indicates that fact 344 was extracted from the words "Drinks occasionally" in the "Social history" section of the text narrative. In some embodiments, visual indicators such as indicators 343 and 345 may be of a different textual and/or graphical style or of a different indicator type than visual indicators such as indicators 313, 315, 317 and 319, to indicate that they correspond to a different fact category. For example, in some embodiments indicators 343 and 345 corresponding to social history fact category 340 may be displayed in a different color than indicators 313, 315, 317 and 319 corresponding to problems fact category 310. In some embodiments, linkages for different individual facts may be displayed in different textual and/or graphical styles or indicator types to allow the user to easily appreciate which fact corresponds to which portion of the text narrative. For example, in some embodiments indicator 343 may be displayed in a different color than indicator 345 because they correspond to different facts, even though both correspond to the same fact category.

In some embodiments, GUI 200 may be configured to allow the user to select one or more of the medical facts in fact panel 230, and in response to the selection, to provide an indication of the portion(s) of the text narrative from which those fact(s) were extracted. An example is illustrated in FIG. 4. In this example, fact 312 ("unspecified chest pain") has been selected by the user in fact panel 230, and in response visual indicator 420 of the portion of the text narrative from which fact 312 was extracted ("chest pain") is provided. Such a user selection may be made in any suitable way, as aspects of the invention are not limited in this respect. Examples include using an input device (e.g., mouse, keyboard, touchpad, stylus, etc.) to click on or otherwise select fact 312, hovering the mouse or other input mechanism above or nearby to fact 312, speaking a selection of fact 312 through voice, and/or any other suitable selection method. Similarly, in some embodiments GUI 200 may be configured to visually indicate the corresponding fact in fact panel 230 when the user selects a portion of the text narrative in text panel 220. In some embodiments, a visual indicator may include a line or other graphical connector between a fact and its corresponding portion of the text narrative. Any visual indicator may be provided in any suitable form (examples of which are given above) as aspects of the invention are not limited in this respect. In addition, aspects of the invention are not limited to visual indicators, as other forms of indicators may be provided. For example, in response to a user selection of fact 312, an audio indicator of the text portion "chest pain" may be provided in some embodiments. In some embodiments, the audio indicator may be provided by playing the portion of the audio recording of the clinician's spoken dictation comprising the words "chest pain". In other embodiments, the audio indicator may be provided by playing an audio version of the words "chest pain" generated using automatic speech synthesis. Any suitable form of indicator or technique for providing indicators may be used, as aspects of the invention are not limited in this respect.

In some embodiments, the set of medical facts corresponding to the current patient encounter (each of which may have been extracted from the text narrative or provided by the user as a discrete structured data item) may be added to an existing electronic medical record (such as an EHR) for patient 122, or may be used in generating a new electronic medical record for patient 122. In some embodiments, clinician 120 and/or coding specialist (or other user) 150 may finally approve the set of medical facts before they are included in any patient record; however, aspects of the present invention are not limited in this respect. In some embodiments, when there is a linkage between a fact in the set and a portion of the text narrative, the linkage may be maintained when the fact is included in the electronic medical record. In some embodiments, this linkage may be made viewable by simultaneously displaying the fact within the electronic medical record and the text narrative (or at least the portion of the text narrative from which the fact was extracted), and providing an indication of the linkage in any of the ways described above. Similarly, extracted facts may be included in other types of patient records, and linkages between the facts in the patient records and the portions of text narratives from which they were extracted may be maintained and indicated in any suitable way.

Figure 7:
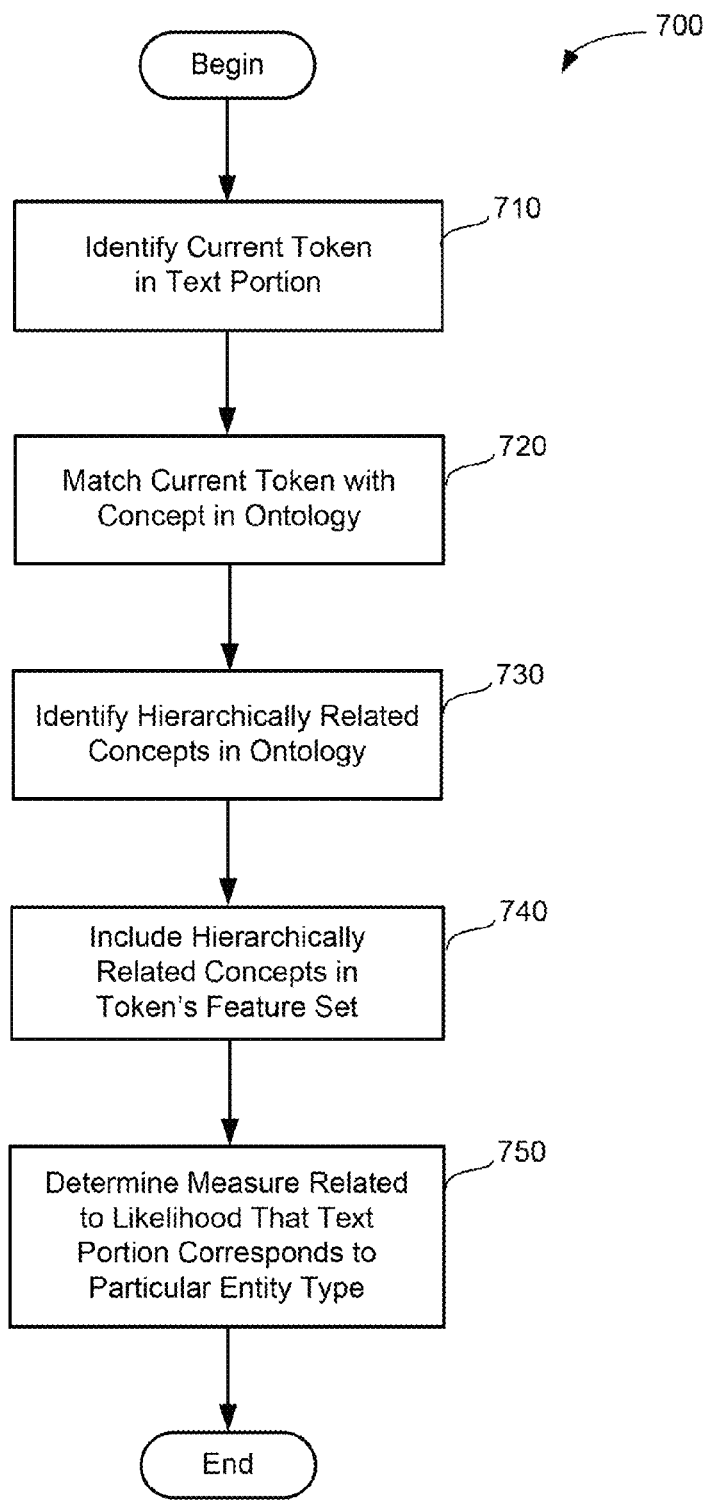
FIG. 7 is a flowchart illustrating an exemplary method for use in entity detection in accordance with some embodiments of the present invention.

It should be appreciated from the foregoing that one embodiment of the invention is directed to a method 700 for entity detection, as illustrated in FIG. 7. Method 700 may be performed, for example, by one or more components of a medical documentation system such as fact extraction component 104, although other implementations are possible and method 700 is not limited in this respect. Method 700 begins at act 710, at which the current token (i.e., the token currently to be processed) in a text portion being considered for entity labeling may be identified. At act 720, the current token may be matched with a matching concept in an ontology. As discussed above, the matching concept may represent a semantic meaning of the current token, and the current token may be one of a set of possible terms for the matching concept. At act 730, a number of concepts hierarchically related to the matching concept may be identified in the ontology. These hierarchically related concepts may be included in the current token's feature set at act 740. Method 700 ends at act 750, at which the feature set may be used to determine a measure related to a likelihood that the text portion including the current token corresponds to a particular entity type.

Figure 8:
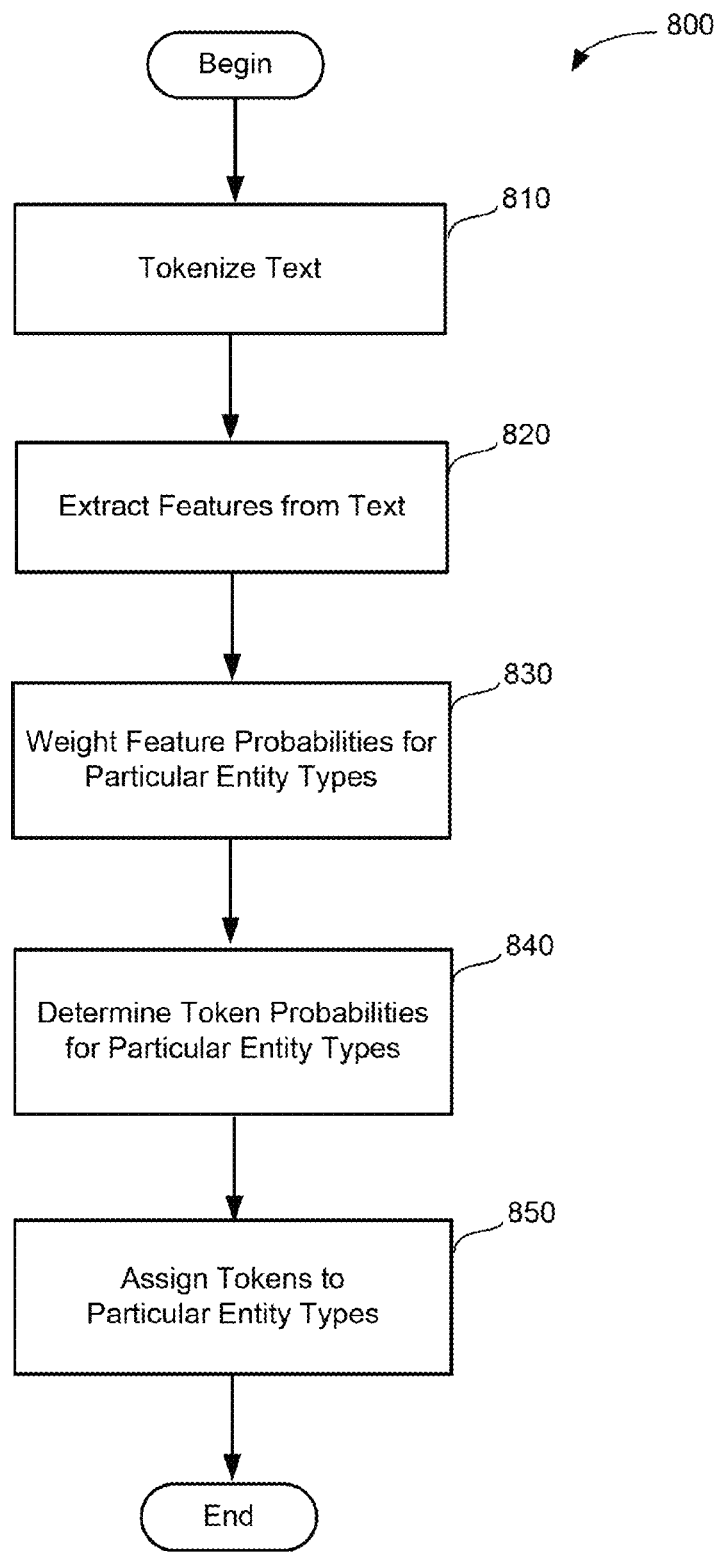
FIG. 8 is a flowchart illustrating an exemplary method for use in entity detection in accordance with some embodiments of the present invention.

It should be appreciated from the foregoing that another embodiment of the invention is directed to a larger method 800 for entity detection, as illustrated in FIG. 8, of which method 700 described above may form a part. Method 800 may be performed, for example, by one or more components of a medical documentation system such as fact extraction component 104, although other implementations are possible and method 800 is not limited in this respect. Method 800 begins at act 810, at which a text to be processed for entity detection may be tokenized. At act 820, features may be extracted for tokens in the text. At act 830, probabilities with which individual extracted features are associated with particular entity types may be weighted with respect to other extracted features. At act 840, the weighted probabilities for features in the extracted feature set for each individual token may be combined to determine probabilities with which individual tokens should be associated with particular entity types. Method 800 ends at act 850, at which the most likely entity type for each token may be identified, and the tokens may be assigned to particular entity types and labeled as such.

Figure 9:
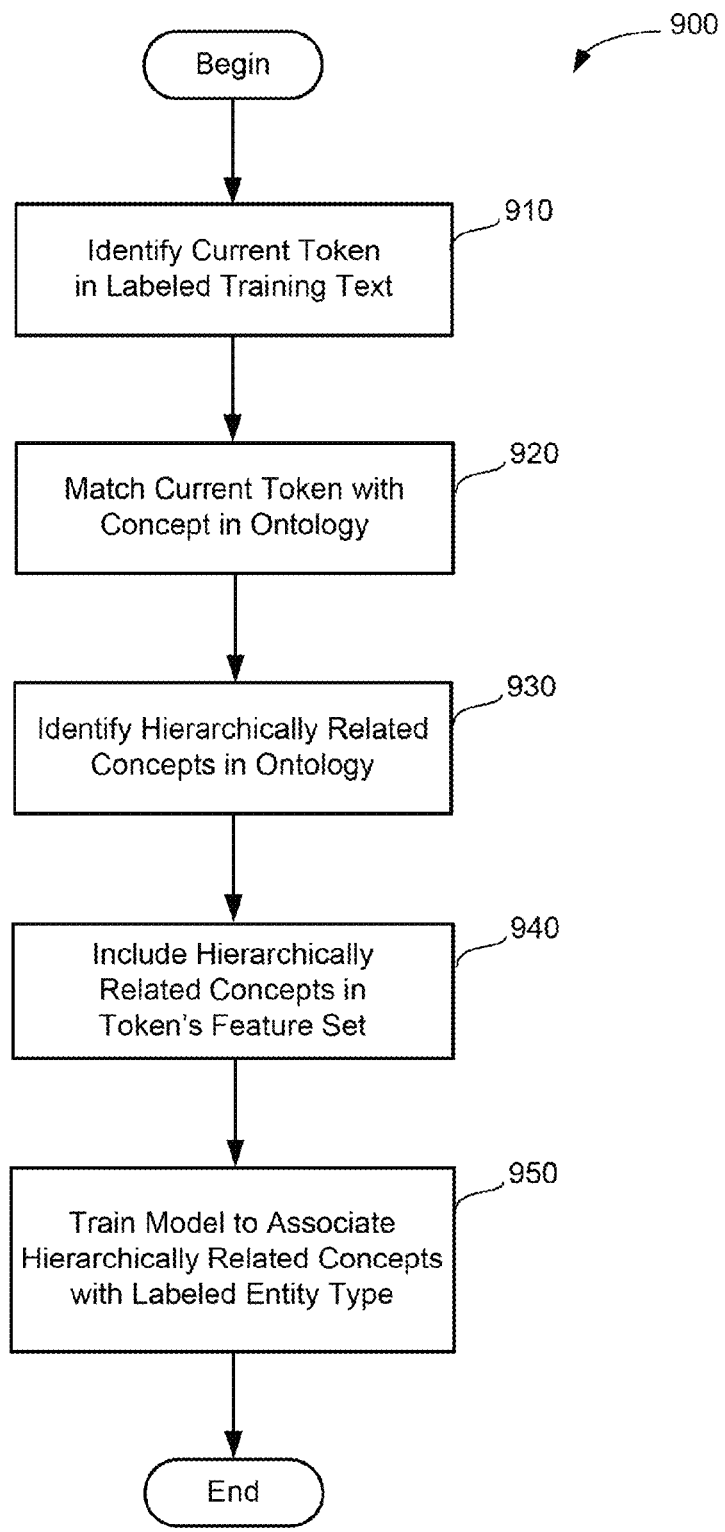
FIG. 9 is a flowchart illustrating an exemplary method for use in training an entity detection model in accordance with some embodiments of the present invention.

It should be appreciated from the foregoing that another embodiment of the invention is directed to a method 900 for training an entity detection model, as illustrated in FIG. 9. Method 900 begins at act 910, at which the current token (i.e., the token currently to be processed) in a training text manually labeled with entity type labels may be identified. At act 920, the current token may be matched with a matching concept in an ontology. As discussed above, the matching concept may represent a semantic meaning of the current token, and the current token may be one of a set of possible terms for the matching concept. At act 930, a number of concepts hierarchically related to the matching concept may be identified in the ontology. These hierarchically related concepts may be included in the current token's feature set at act 940. Method 900 ends at act 950, at which the feature set may be used to train the entity detection model to associate the hierarchically related concepts with the entity type with which the current token was labeled. As discussed above, in some embodiments, the statistical entity detection model may be trained to associate each of the hierarchically related concepts with a probability of corresponding to the labeled entity type. In some embodiments, the model may be further trained to weight the hierarchically related concepts with respect to other token features to optimize a likelihood of labeling a text portion including the current token as corresponding to the labeled entity type.

Figure 10:
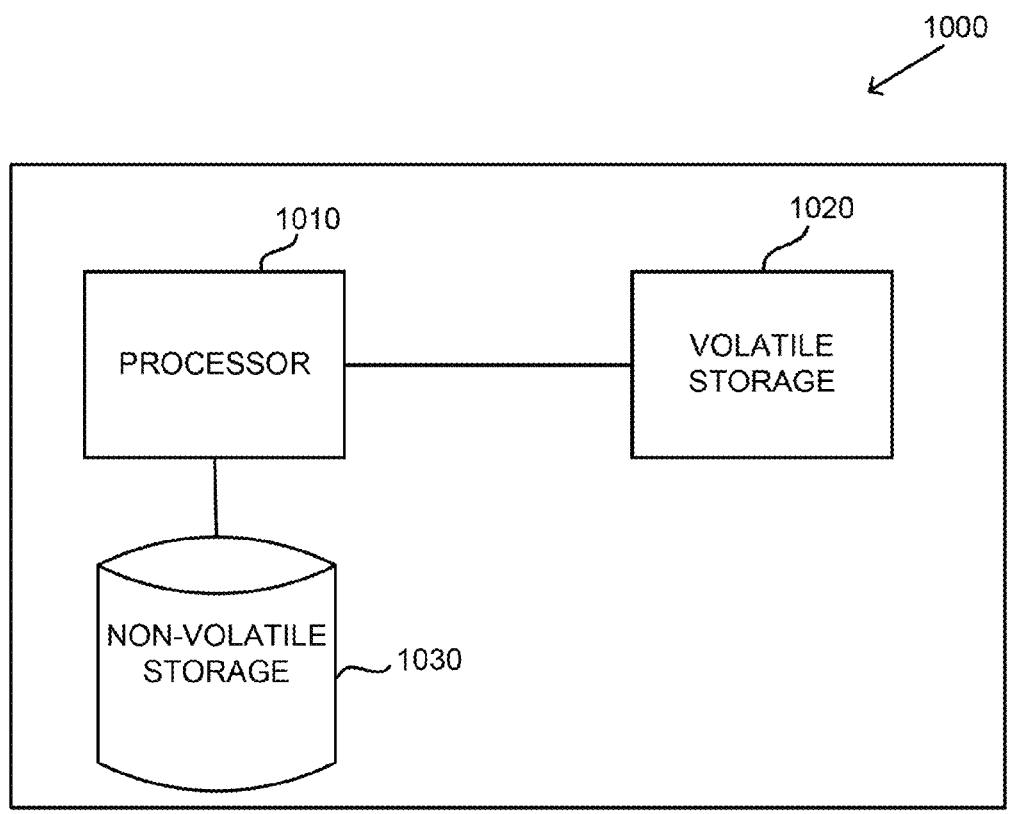
FIG. 10 is a block diagram of an exemplary computer system on which aspects of the present invention may be implemented.

An entity detection and/or entity detection training system in accordance with the techniques described herein may take any suitable form, as aspects of the present invention are not limited in this respect. An illustrative implementation of a computer system 1000 that may be used in connection with some embodiments of the present invention is shown in FIG. 10. One or more computer systems such as computer system 1000 may be used to implement any of the functionality described above. The computer system 1000 may include one or more processors 1010 and one or more tangible, non-transitory computer-readable storage media (e.g., volatile storage 1020 and one or more non-volatile storage media 1030, which may be formed of any suitable non-volatile data storage media). The processor 1010 may control writing data to and reading data from the volatile storage 1020 and the non-volatile storage device 1030 in any suitable manner, as the aspects of the present invention are not limited in this respect. To perform any of the functionality described herein, the processor 1010 may execute one or more instructions stored in one or more computer-readable storage media (e.g., volatile storage 1020), which may serve as tangible, non-transitory computer-readable storage media storing instructions for execution by the processor 1010.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of embodiments of the present invention comprises at least one computer-readable storage medium (i.e., a tangible, non-transitory computer-readable medium, such as a computer memory, a floppy disk, a compact disk, a magnetic tape, or other tangible, non-transitory computer-readable medium) encoded with a computer program (i.e., a plurality of instructions), which, when executed on one or more processors, performs above-discussed functions of embodiments of the present invention. The computer-readable storage medium can be transportable such that the program stored thereon can be loaded onto any computer resource to implement aspects of the present invention discussed herein. In addition, it should be appreciated that the reference to a computer program which, when executed, performs any of the above-discussed functions, is not limited to an application program running on a host computer. Rather, the term "computer program" is used herein in a generic sense to reference any type of computer code (e.g., software or microcode) that can be employed to program one or more processors to implement above-discussed aspects of the present invention.

The phraseology and terminology used herein is for the purpose of description and should not be regarded as limiting. The use of "including," "comprising," "having," "containing", "involving", and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements from each other.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A method comprising:
   matching a token from at least a portion of a text string with a matching concept in an ontology;
   identifying a first concept as being hierarchically related to the matching concept within the ontology;
   identifying a second concept as being hierarchically related to the first concept within the ontology;
   including the first and second concepts in a set of features of the token; and
   determining, using at least one processor, a measure related to a likelihood that the at least a portion of the text string corresponds to a particular entity type, based at least in part on the set of features of the token.

2. The method of claim 1, wherein the particular entity type is a particular type of medical fact.

3. The method of claim 1, wherein the first concept is an ancestor of the matching concept within the ontology.

4. The method of claim 3, wherein the second concept is an ancestor of the first concept within the ontology.

5. The method of claim 4, wherein the first concept is a parent concept of the matching concept within the ontology, and wherein the second concept is a parent concept of the first concept within the ontology.

6. The method of claim 1, wherein the matching concept represents a semantic meaning of the token.

7. The method of claim 1, wherein the determining comprises inputting the first and second concepts, as features of the token, to a statistical model trained to determine the measure based on a plurality of features of the token.

8. The method of claim 1, wherein the determining comprises weighting the first and second concepts as features of the token relative to other features of the token.

9. Apparatus comprising:
   at least one processor; and
   at least one processor-readable storage medium storing processor-executable instructions that, when executed by the at least one processor, perform a method comprising:
   matching a token from at least a portion of a text string with a matching concept in an ontology;
   identifying a first concept as being hierarchically related to the matching concept within the ontology;
   identifying a second concept as being hierarchically related to the first concept within the ontology;
   including the first and second concepts in a set of features of the token; and
   determining a measure related to a likelihood that the at least a portion of the text string corresponds to a particular entity type, based at least in part on the set of features of the token.

10. The apparatus of claim 9, wherein the particular entity type is a particular type of medical fact.

11. The apparatus of claim 9, wherein the first concept is a parent concept of the matching concept within the ontology, and wherein the second concept is a parent concept of the first concept within the ontology.

12. The apparatus of claim 9, wherein the determining comprises inputting the first and second concepts, as features of the token, to a statistical model trained to determine the measure based on a plurality of features of the token.

13. At least one computer-readable storage medium encoded with computer-executable instructions that, when executed, perform a method comprising:

matching a token from at least a portion of a text string with a matching concept in an ontology;

identifying a first concept as being hierarchically related to the matching concept within the ontology;

identifying a second concept as being hierarchically related to the first concept within the ontology;

including the first and second concepts in a set of features of the token; and determining a measure related to a likelihood that the at least a portion of the text string corresponds to a particular entity type, based at least in part on the set of features of the token.

14. The at least one computer-readable storage medium of claim 13, wherein the particular entity type is a particular type of medical fact.

15. The at least one computer-readable storage medium of claim 13, wherein the first concept is an ancestor of the matching concept within the ontology.

16. The at least one computer-readable storage medium of claim 15, wherein the second concept is an ancestor of the first concept within the ontology.

17. The at least one computer-readable storage medium of claim 16, wherein the first concept is a parent concept of the matching concept within the ontology, and wherein the second concept is a parent concept of the first concept within the ontology.

18. The at least one computer-readable storage medium of claim 13, wherein the matching concept represents a semantic meaning of the token.

19. The at least one computer-readable storage medium of claim 13, wherein the determining comprises inputting the first and second concepts, as features of the token, to a statistical model trained to determine the measure based on a plurality of features of the token.

20. The at least one computer-readable storage medium of claim 13, wherein the determining comprises weighting the first and second concepts as features of the token relative to other features of the token.

* * * * *